(12) United States Patent
Blain et al.

(10) Patent No.: US 8,062,304 B2
(45) Date of Patent: Nov. 22, 2011

(54) SPINAL IMPLANT DISTRACTOR/INSERTER

(75) Inventors: Jason Blain, Encinitas, CA (US); Dean Johnson, Solana Beach, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 1212 days.

(21) Appl. No.: 11/740,242

(22) Filed: Apr. 25, 2007

(65) Prior Publication Data

US 2008/0269764 A1 Oct. 30, 2008

(51) Int. Cl.
*A61B 17/58* (2006.01)
*A61B 17/60* (2006.01)
(52) U.S. Cl. .......................... 606/90; 606/99; 606/86 A
(58) Field of Classification Search ............... 606/90, 606/99, 86 A
See application file for complete search history.

(56) References Cited

U.S. PATENT DOCUMENTS

| | | | |
|---|---|---|---|
| 3,486,505 A | 12/1969 | Morrison | |
| 5,122,130 A | 6/1992 | Keller | |
| 5,235,966 A | 8/1993 | Jamner | |
| 5,431,658 A | 7/1995 | Moskovich | |
| 6,004,326 A | 12/1999 | Castro et al. | |
| 6,015,426 A * | 1/2000 | Griffiths | 606/205 |
| 6,096,038 A | 8/2000 | Michelson | |
| 6,179,873 B1 | 1/2001 | Zientek | |
| 6,224,599 B1 | 5/2001 | Baynham et al. | |
| 6,332,887 B1 | 12/2001 | Knox | |
| 6,478,800 B1 | 11/2002 | Fraser et al. | |
| 6,652,533 B2 | 11/2003 | O'Neil | |
| 6,752,832 B2 | 6/2004 | Neumann | |
| 6,755,841 B2 | 6/2004 | Fraser et al. | |
| 7,018,416 B2 | 3/2006 | Hanson et al. | |
| 7,211,085 B2 | 5/2007 | Michelson | |
| 2002/0082695 A1 | 6/2002 | Neumann | |
| 2002/0116009 A1 | 8/2002 | Fraser et al. | |
| 2003/0028197 A1 | 2/2003 | Hanson et al. | |
| 2003/0199874 A1 | 10/2003 | Michelson | |
| 2004/0002758 A1 | 1/2004 | Landry et al. | |
| 2004/0030387 A1 | 2/2004 | Landry et al. | |
| 2004/0225295 A1 | 11/2004 | Zubok et al. | |
| 2005/0165408 A1 | 7/2005 | Puno et al. | |
| 2005/0192587 A1 * | 9/2005 | Lim | 606/86 |
| 2006/0241641 A1 | 10/2006 | Albans et al. | |
| 2007/0233153 A1 * | 10/2007 | Shipp et al. | 606/99 |
| 2009/0005784 A1 * | 1/2009 | Blain et al. | 606/90 |

OTHER PUBLICATIONS

Synthes Spine Brochure "Luminary™ Alif. Disc Preparation and implant insertion instruments," 2006.

* cited by examiner

*Primary Examiner* — Thomas C. Barrett
*Assistant Examiner* — Michael T. Schaper
(74) *Attorney, Agent, or Firm* — Knobbe, Martens, Olson & Bear, LLP.

(57) ABSTRACT

A vertebral distractor-inserter comprising a housing, a pair of opposing arms in mechanical communication with the housing, a driving rod extending through at least a portion of the housing and between the arms, wherein the driving rod comprises an axis and a surface with a plurality of angled ratchet teeth on at least a portion of the surface, and a ratchet drive mechanism in mechanical communication with the driving rod. A vertebral distractor-inserter comprising a pair of opposing arms, a housing in mechanical communication with the arms and rotatable about an axis extending between the arms, and a driving rod extending through at least a portion of the housing and between the arms. A vertebral distractor-inserter adapted for single-handed use. A vertebral distractor-inserter having an implant depth adjustor. Methods for distracting adjacent vertebrae and inserting an implant using the devices described herein.

24 Claims, 14 Drawing Sheets

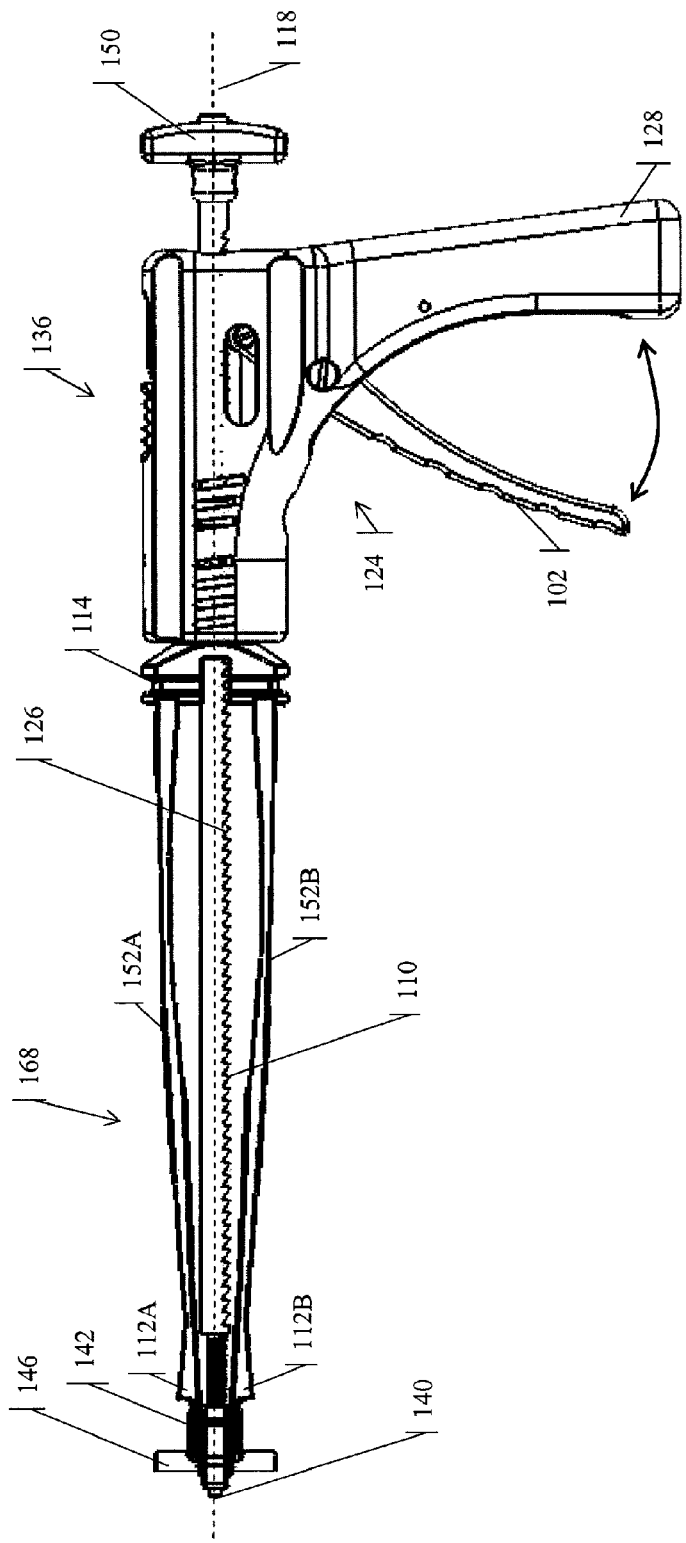
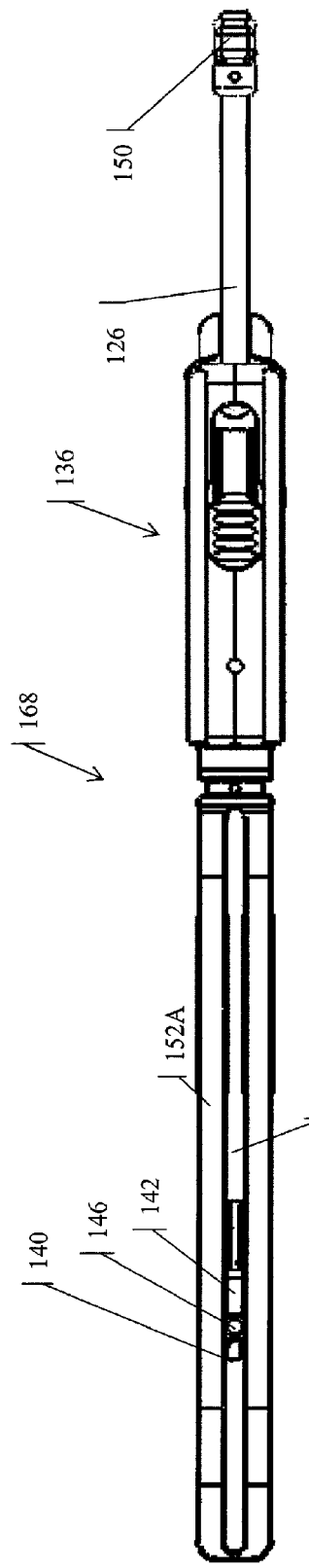
Figure 1B
Figure 1C

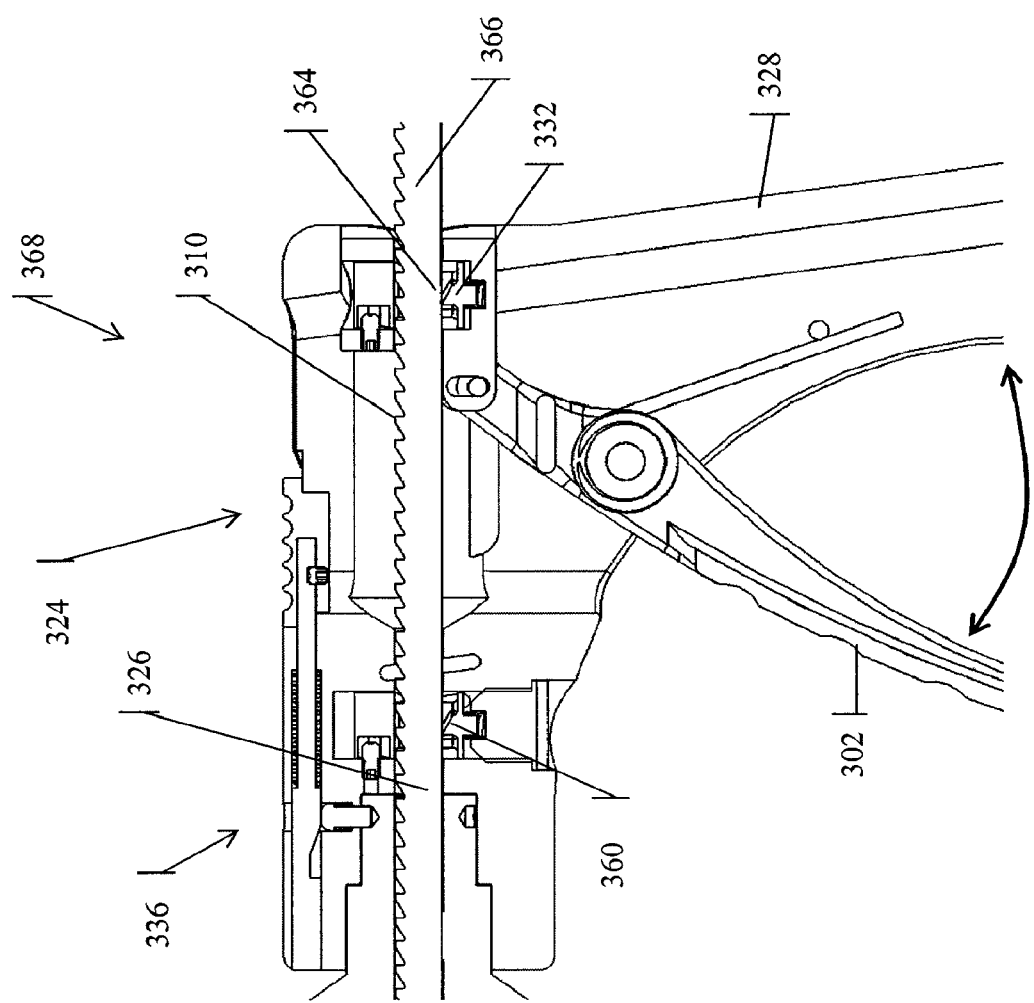

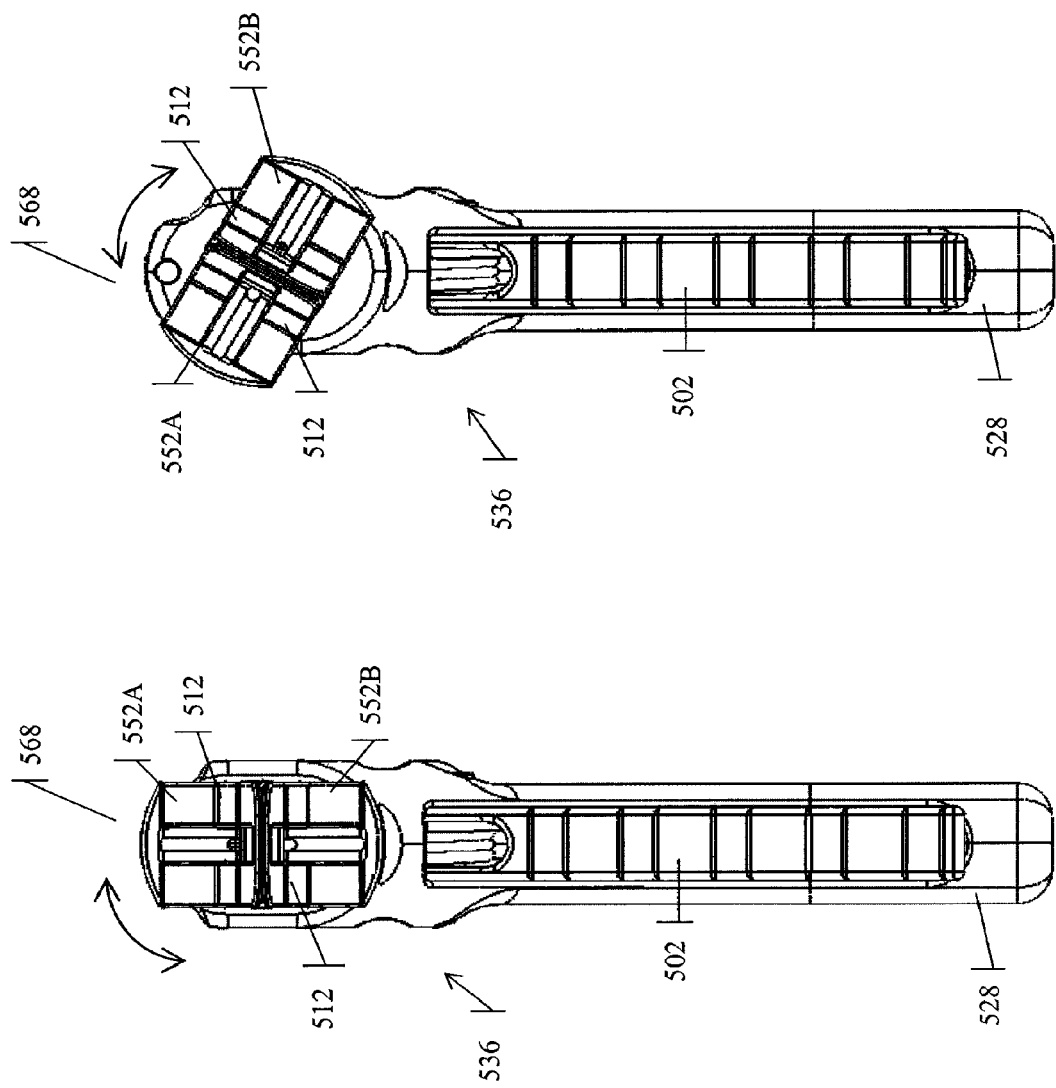

SPINAL IMPLANT DISTRACTOR/INSERTER

BACKGROUND OF THE INVENTION

Spinal disc replacement and/or spinal fusion are sometimes necessary for patients having lumbar degenerative disc disease. It has been estimated that at least 30% of people aged 30 to 50 will have some degree of disc space degeneration, although not all will have pain or ever be diagnosed formally with degenerative disc disease. After a patient reaches 60, it is more normal than not to have some level of disc degeneration. A twisting injury often starts degenerative disc disease, but it can also be initiated by everyday wear and tear on the spine.

Lower back pain is the most common symptom of a compromised disc emblematic of degenerative disc disease. For most patients with lumbar degenerative disc disease, the pain is for the most part tolerable and low-grade, but continuous with occasional flaring of intense pain. Pain can be simply centered on the lower back, or it can radiate to the hips and legs. It can get worse by sitting, or it can be intensified by twisting, lifting, or bending. For some, the pain from the disease decreases over time, since a fully degenerated disc has no pain-causing inflammatory proteins, and the disc usually collapses into a stable position-eliminating the micro-motion that often generates the pain.

For many, non-surgical care can successfully treat the symptoms associated with degenerative disc disease. Doctors will often prescribe a regimen of anti-inflammatory medication, pain medication (injected or oral), exercise, physical therapy, and/or chiropractic manipulation. For others, however, surgery is the best option for treatment once the non-surgical care has not resulted in relief and/or the patient's normal activities have been significantly constrained by his symptoms.

One option for surgical relief is lumbar spinal fusion surgery. This treatment stops motion at the painful segment of the spine by fusing two or more vertebrae. Depending on how many segments of the spine need fusion, and which specific spine segments are to be fused, this surgery may remove some of the normal motion of the spine. Additionally, where multiple segments are fused, back movement may be significantly diminished, and may itself cause pain (fusion disease). Nevertheless, single-level fusion at the L5-S1 segment, the most likely level to break down for degenerative disc disease, for example, does not significantly change the mechanics in the back and is the most common form of fusion. While lumbar spinal fusion surgery is a major surgery, it can be an effective option for patients to enhance their activity level and overall quality of life, particularly when performed using minimally invasive techniques. However, while spinal fusion surgery has its benefits, and is effective in carefully selected patients, the cost of this success is the risk of accelerated degenerative change at adjacent segments.

Thus, another option to treat lumbar degenerative disc disease through surgery is disc replacement using either an artificial disc, a bone graft from the patient's own iliac crest, or a cadaver bone. One potential benefit of disc replacement is the decreased risk of adjacent segment degeneration. It is postulated that replacing the disc, instead of fusing adjacent vertebrae together, maintains more of the lumbar spine normal motion, thereby reducing the chance that adjacent levels of the spine will break down due to increased stress.

The standard surgical procedure for disc replacement approaches the cervical disc from the front (i.e. anterior approach). The entire worn-out disc is removed. A replacement disc is placed into the intervertebral disc space after the worn-out disc is removed. One goal of this procedure is retention of as much normal motion as possible, while keeping the motion segment stable.

As currently practiced, replacement surgery and spinal fusion from the anterior approach require simultaneous use of multiple tools to keep the spine exposed, to prepare the site for implantation, to distract the vertebrae, and to implant the new disc or graft in the vertebral space at the proper orientation and to the desired depth. For example, several tools are often used to prepare the intervertebral space through removal of the cartilaginous endplates of the vertebral bodies. These tools may include rongeurs, rasps, and curettes. Another tool, such as a sizing gauge, might be used to determine the appropriate position and size of the implant to be used. Another tool is used to distract the vertebrae. While this distracting tool is holding the vertebrae apart, yet another tool may be used to place the implant in the distracted space. In some instances, a slap-hammer type tool, or an impact-type driver is used to place the implant between the vertebrae, or to prepare the intervertebral space for the implant.

There is a need for improved tools to aid in disc replacement and/or spinal fusion, which allow a spinal surgeon to more easily access and position a replacement disc or bone graft within the vertebral space. Additionally there is a need for tools that allow a spinal surgeon to control the implantation depth of a replacement disc or bone graft. There is also a need for a tools that are multifunctional and allow for single-handed operation to reduce the number of tools required for performing multiple functions during disc replacement surgery or during spinal fusion surgery and to improve the ease and speed with which disc replacement and/or spinal fusion can be completed.

SUMMARY OF THE INVENTION

The foregoing and additional needs are met by embodiments of the invention, which provide a vertebral distractor-inserter (i.e. device), comprising a pair of opposing arms, a driving rod extending through at least a portion of the housing and between the pair of opposing arms. In some embodiments, the driving rod comprises an axis and a surface with a plurality of angled ratchet teeth on at least a portion of the surface, and a ratchet drive mechanism in mechanical communication with the driving rod. In some embodiments, the vertebral distractor-inserter comprises a housing in mechanical communication with the pair of opposing arms. In some embodiments, the vertebral distractor-inserter (i.e. device) comprises a handle attached to the housing. The terms "vertebral distractor-inserter," "distractor-inserter," and "device" are interchangeable as used herein.

In some embodiments, the vertebral distractor-inserter comprises a ratchet drive mechanism comprising an activating lever mounted to the housing by an activating lever pivot, a first ratchet pawl coupled to the activating lever and adapted to engage the ratchet teeth and move the driving rod distally relative to the housing, and a second ratchet pawl adapted to engage the ratchet teeth and oppose proximal motion of the driving rod relative to the housing.

In some embodiments, the vertebral distractor-inserter comprises a ratchet drive mechanism comprising an activating lever mounted to the housing by an activating lever pivot, a first ratchet pawl coupled to the activating lever and adapted to engage the ratchet teeth and move the driving rod distally relative to the housing, and an engaging element to oppose proximal motion of the driving rod relative to the housing.

In some embodiments the ratchet drive mechanism comprises an activating lever spring coupled to the activating lever and the handle, wherein the activating lever spring opposes proximal movement of the lever relative to the handle. In some embodiments of the distractor-inserter, the ratchet drive mechanism comprises a first pawl spring that opposes downward movement of the first pawl and a second pawl spring that opposes downward movement of the second pawl.

In some embodiments of the distractor-inserter, the driving rod comprises a distal end and an implant interface coupled to the distal end of the driving rod.

In some embodiments, the distractor-inserter comprises an implant in contact with the implant interface, whereby distal motion of the driving rod imparts distal motion to the implant through the implant interface; and distal motion of the implant forces the opposing arms apart.

In some embodiments, each opposing arm comprises an arm pivot. Some embodiments comprise a pair of opposing arms comprising an arm spring. Some embodiments comprise an arm comprising an arm depth guard. In some embodiments, the implant interface comprises an implant coupler.

In some embodiments, the vertebral distractor-inserter is adapted for single-handed use.

In some embodiments, the surface of the driving rod comprises an area that is substantially free of ratchet teeth on a contiguous longitudinal surface of the driving rod, and the driving rod is movable proximally relative to the housing upon rotation of the rod about its axis such that the ratchet pawls are in contact with the contiguous longitudinal surface that is free of ratchet teeth. In some embodiments, the ratchet teeth disengage from first and second ratchet pawls upon rotation of the driving rod about its axis. In some embodiments, the driving rod comprises a proximal end having a knob.

Some embodiments of the vertebral distractor-inserter comprise a drive mechanism comprising at least one gripping element which opposes proximal motion of the drive mechanism. The drive mechanism having a gripping element may additionally comprise at least one gripping spring.

In some embodiments of the distractor-inserter, the drive mechanism comprises a gripping element and a ratcheting drive mechanism as described previously. Some embodiments comprise other means for driving implant distally. These means can be other mechanical mechanisms capable of imparting unidirectional movement, along with a release mechanism for reversing such unidirectional movement. Some embodiments comprise other means for distracting the arms. For example, the arms may be distracted by a built-in distracting member, such as in implant interface adapted to force the arms apart.

In some embodiments, the vertebral distractor-inserter comprises a pair of opposing arms, a housing in mechanical communication with the pair of opposing arms and rotatable about an axis extending between the opposing arms, and a driving rod extending through at least a portion of the housing and between the pair of opposing arms. Some embodiments comprise a distal end having an implant interface, wherein the housing and at least a portion of the driving rod are rotatable relative to the pair of opposing arms and the implant interface. Some embodiments further comprise an implant interface comprising an interface rotation element, whereby the interface rotation element allows rod rotation relative to the pair of opposing arms. Some embodiments further comprise a housing comprising a housing rotation element, whereby the housing rotation element allows housing and rod rotation relative to the pair of opposing arms.

In some embodiments, the vertebral distractor-inserter comprises a pair of opposing arms, a housing in mechanical communication with the pair of opposing arms and rotatable about an axis extending between the opposing arms, a driving rod extending through at least a portion of the housing and between the pair of opposing arms, and a drive mechanism adapted to move the driving rod distally relative to the housing.

In some embodiments of a rotatable vertebral distractor-inserter, the vertebral distractor-inserter comprises a drive mechanism. Embodiments of the drive mechanism are described herein.

In some embodiments, the invention provides a vertebral distractor-inserter comprising a housing, a pair of opposing arms in mechanical communication with the housing, a driving rod extending through at least a portion of the housing and between the pair of opposing arms, a drive mechanism adapted to move the driving rod distally relative to the housing, and an implant depth adjustor that is adjustable to a plurality of implant depth settings and is adapted to push the distractor-inserter proximally upon insertion of an implant to a selected implant depth setting. The implant depth adjustor may optionally comprise an implant depth stop. Example drive mechanisms are described herein. This vertebral distractor-inserter may be ratcheting, gripping, a combination of these, etc. Any distractor-inserter described herein may be adapted for single-handed use. It may also or alternatively comprise an implant interface as described herein. It may also be adapted such that the housing and at least a portion of the driving rod are rotatable about an axis extending between the opposing arms, as described herein.

In some embodiments, the invention provides a method for distracting adjacent vertebrae and inserting an implant between the distracted vertebrae. The method comprises mounting the implant to a driving rod of a vertebral distractor-inserter having a housing, a pair of opposing arms in mechanical communication with the housing and having a distal end, and a drive mechanism in mechanical communication with the driving rod, wherein the driving rod extends through at least a portion of the housing and between the pair of opposing arms. The method further comprises positioning the distal end of the pair of arms between the vertebrae, distracting the vertebrae by single-handed operation of the vertebral distractor-inserter, inserting the implant between the distracted vertebrae by single-handed operation of the vertebral distractor-inserter, and retracting the pair of opposing arms from between the vertebrae.

In some embodiments, the invention further provides a method for distracting adjacent vertebrae and inserting an implant between the distracted vertebrae, wherein the distracting comprises activating the drive mechanism using one hand, and wherein the activating moves the implant distally and distracts the pair of opposing arms. In some embodiments, insertion comprises advancing the implant into the distracted space between the vertebrae. In some embodiments advancing the implant comprises activating the drive mechanism using one hand and extending the implant beyond the distal end of the pair of opposing arms. In some embodiments, the method comprises the additional step of releasing the implant from the distractor-inserter.

In some embodiments of the method for distracting adjacent vertebrae and inserting an implant between the distracted vertebrae, the method comprises urging the pair of arms between the vertebrae up to the position where a depth guard of the arms contacts the vertebrae. In some embodiments, the method comprises urging the pair of arms between the vertebrae up to a distal depth of at most about 75 mm, or at least about 25 mm, or between about 35 mm and 55 mm. When referring to distal depth herein, "about" refers to variations in depth of between 1 mm and 2 mm, or between 2 mm and 5 mm. In some embodiments, the distal depth is the distance from the depth guard to the distal end of the pair of opposing arms. In some embodiments, the arms are inserted between the vertebrae up to a distal depth such that the depth guard is proximal to, but not abutting, the proximal side of the vertebrae. In some embodiments, the depth guard is proximal to and abutting, or contacting, the proximal side of the vertebrae.

In some embodiments, mounting the implant comprises the step of adjusting the implant depth adjustor to control the maximum implant depth achievable during the inserting step. In a related embodiment, the implant depth achievable is a maximum of about 25 mm, a minimum of about 0 mm, or between about 3 mm and 8 mm. When referring to implant herein, "about" refers to variations in depth of between 1 mm and 2 mm, or between 2 mm and 5 mm. The implant depth is measured from the distal end of the depth stop to the distal end of the implant interface.

In some embodiments insertion of the implant comprises the step of retracting the pair of opposing arms from between the vertebrae by abutting the implant depth adjustor against a proximal side of the vertebrae and activating the drive mechanism using one hand.

In some embodiments, the invention provides a method comprising activating the drive mechanism comprising the step of ratcheting the driving rod distally. In some such embodiments, the driving rod comprises an axis and a surface with a plurality of angled ratchet teeth on at least a portion of the surface. In some embodiments, the drive mechanism comprises an activating lever capable of movement between a first position and a second position and mounted to the housing by an activating lever pivot. In some embodiments, the drive mechanism further comprises a first ratchet pawl coupled to the activating lever and adapted to engage the ratchet teeth and move the driving rod distally relative to the housing, and a second ratchet pawl adapted to engage the ratchet teeth and oppose proximal motion of the driving rod relative to the housing.

In some embodiments, the invention provides a method comprising gripping the rod and moving the driving rod distally wherein the distractor-inserter is an embodiment as described herein. In some embodiments, the step of ratcheting comprises the step of applying a force to the activating lever to move the lever toward the second position. In some embodiments, wherein the drive mechanism comprises a handle attached to the housing and an activating lever spring coupled to the activating lever and the handle, and wherein the activating lever spring opposes proximal movement of the lever relative to the handle, the step of ratcheting further comprises the steps of releasing the force on the activating lever and allowing the activating lever spring to move the activating lever toward the first position.

In some embodiments, the invention further provides a method comprising rotating the housing and at least a portion of the driving rod relative to the pair of opposing arms and to the implant, wherein the housing is rotatable about an axis extending between the opposing arms relative to the arms and to the implant, and wherein at least a portion of the driving rod is rotatable about the axis extending between the opposing arms relative to the pair of opposing arms and to the implant. This method may further comprise activating a drive mechanism wherein the activating moves the implant distally and distracts the pair of opposing arms. In some embodiments the step of inserting the implant comprises advancing the implant into the distracted space between the vertebrae. In some embodiments of the method for distracting adjacent vertebrae and inserting an implant between the distracted vertebrae, the advancing step comprises activating the drive mechanism and extending the implant beyond the distal end of the pair of opposing arms.

In some embodiments, the invention provides a method comprising mounting the implant to a driving rod of a vertebral distractor-inserter having a housing, a pair of opposing arms, and a ratchet drive mechanism in mechanical communication with the driving rod, wherein the driving rod extends through at least a portion of the housing and between the pair of opposing arms, positioning the distal end of the pair of arms between the vertebrae, distracting the vertebrae, wherein the distracting comprises activating the ratchet drive mechanism, inserting the implant between the distracted vertebrae, wherein the inserting comprises advancing the implant into the distracted space between the vertebrae, and wherein the advancing comprises activating the ratchet drive mechanism, and retracting the pair of opposing arms from between the vertebrae.

In some embodiments, the activating step moves the implant distally and distracts the pair of opposing arms. In some embodiments, advancing the implant comprises extending the implant beyond the distal end of the pair of opposing arms. In some embodiments, the activating the ratchet drive mechanism comprises ratcheting the driving rod distally, wherein the driving rod comprises an axis and a surface with a plurality of angled ratchet teeth on at least a portion of the surface, and wherein the ratchet drive mechanism comprises an activating lever capable of movement between a first position and a second position and mounted to the housing by an activating lever pivot, a first ratchet pawl coupled to the activating lever and adapted to engage the ratchet teeth and move the driving rod distally relative to the housing, and a second ratchet pawl adapted to engage the ratchet teeth and oppose proximal motion of the driving rod relative to the housing.

In some embodiments, the invention provides a method comprising a step of applying a force to the activating lever to move the lever from a first position toward a second position. In some embodiments the drive mechanism comprises a handle attached to the housing and an activating lever spring coupled to the activating lever and the handle, wherein the activating lever spring opposes proximal movement of the lever relative to the handle. In some embodiments, the step of ratcheting further comprises the steps of releasing the force on the activating lever and allowing the activating lever spring to move the activating lever toward the first position. In some embodiments wherein the implant was coupled to the distractor-inserter, the method comprises releasing the implant from the distractor-inserter.

In some embodiments, the invention provides a method comprising mounting the implant to a driving rod of a vertebral distractor-inserter having a pair of opposing arms having a distal end, a housing in mechanical communication with the pair of opposing arms which is rotatable about an axis extending between the opposing arms relative to the arms and to the implant, and a drive mechanism in mechanical communication with the driving rod, wherein the driving rod extends through at least a portion of the housing and between the pair of opposing arms and wherein at least a portion of the driving rod is rotatable about the axis extending between the opposing arms relative to the pair of opposing arms and to the implant, positioning the distal end of the pair of arms between the vertebrae, rotating the housing and at least a portion of the driving rod relative to the pair of opposing arms and to the implant, distracting the vertebrae, inserting the implant between the distracted vertebrae, and retracting the pair of opposing arms from between the vertebrae. The distracting may further comprise activating the drive mechanism, wherein the activating step comprises moving the implant distally and distracting the pair of opposing arms. Inserting the implant may comprise advancing the implant into the distracted space between the vertebrae. Advancing the implant may comprise activating the drive mechanism and extending the implant beyond the distal end of the pair of opposing arms.

The method may further comprise ratcheting the driving rod distally, wherein the driving rod comprises an axis and a surface with a plurality of angled ratchet teeth on at least a portion of the surface, and wherein the drive mechanism comprises an activating lever capable of movement between a first position and a second position and mounted to the housing by an activating lever pivot, a first ratchet pawl coupled to the activating lever and adapted to engage the ratchet teeth and move the driving rod distally relative to the housing, and a second ratchet pawl adapted to engage the ratchet teeth and oppose proximal motion of the driving rod relative to the housing. The ratcheting can comprise actions previously described herein.

Positioning the implant can further comprise using a depth adjustor to control the implantation depth between the vertebrae. Some embodiments of the method comprise mounting the implant to a driving rod of a vertebral distractor-inserter having a pair of opposing arms having a distal end and a depth guard, an implant depth adjustor that is adjustable to a plurality of implant depth settings, a housing in mechanical communication with the pair of opposing arms, and a drive mechanism in mechanical communication with the driving rod, wherein the driving rod extends through at least a portion of the housing and between the pair of opposing arms, and wherein the mounting comprises the step of adjusting the implant depth adjustor to control the maximum distal implant depth achievable during the inserting step, positioning the distal end of the pair of arms between the vertebrae, wherein the positioning comprises urging the pair of arms between the vertebrae up to the position where the depth guard contacts the vertebrae, distracting the vertebrae, inserting the implant between the distracted vertebrae, and retracting the pair of opposing arms from between the vertebrae.

In some embodiments, the invention provides a method comprising urging the pair of arms between the vertebrae. The step of urging is capable of moving the pair of arms between the vertebrae up to a distal depth of at most about 75 mm, or at least about 25 mm, or between about 35 mm and 55 mm. When referring to distal depth herein, "about" refers to variations in depth of between 1 mm and 2 mm, or between 2 mm and 5 mm. In some embodiments, the distal depth is the distance from the depth guard to the distal end of the pair of opposing arms. In some embodiments, the arms are inserted between the vertebrae up to a distal depth such that the depth guard is proximal to, but not abutting, the proximal side of the vertebrae. In some embodiments, the depth guard is proximal to and abutting, or contacting, the proximal side of the vertebrae.

In some embodiments, the implant depth achievable is a maximum of about 25 mm, a minimum of about 0 mm, or between about 3 mm and 8 mm. When referring to implant herein, "about" refers to variations in depth of between 1 mm and 2 mm, or between 2 mm and 5 mm. The implant depth is measured from the distal end of the depth stop to the distal end of the implant interface.

In some embodiments, the distractor-inserter has a housing and is adapted to push the housing proximally upon insertion of the implant to a selected implant depth setting, and the inserting comprises the step of retracting the pair of opposing arms from between the vertebrae by abutting the arm depth guard against a proximal side of the vertebrae and activating the drive mechanism.

In some embodiments, the invention provides a vertebral distractor-inserter, comprising a housing, a pair of opposing arms in mechanical communication with the housing, and a driving means for driving a rod and an implant at the distal end of the rod distally, wherein the driving means comprises an activating lever and a driving mechanism activated by the activating lever. The driving means may comprise a gripping means for gripping the rod while the activating lever drives the rod distally relative to the housing. The driving means may comprise a ratcheting means for incrementally ratcheting the rod distally as the activating lever is pulled proximally relative to the housing. The vertebral distractor-inserter may comprise a holding means for opposing proximal motion of the rod while resetting the lever after lever activation. The vertebral distractor-inserter may comprise a rotating means for allowing operator rotation of the housing relative to the pair of opposing arms about an axis extending between the opposing arms. The vertebral distractor-inserter may comprise a depth-controlling means for adjusting and controlling the depth to which an implant may be inserted by an operator between adjacent vertebrae.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A & 1B: Depict external views of an embodiment of a device according to the present invention.

FIG. 1C: Provides a top view of an embodiment of a device according to the present invention.

FIG. 3B: Provides a cutaway side view the housing of an embodiment of the device having ratchet teeth disengaged for retraction of the driving rod.

FIGS. 5A & 5B: Depict views of an embodiment of the device showing relative rotation of the arms and the handle.

DETAILED DESCRIPTION OF THE INVENTION

The invention disclosed herein provides a tool to aid in intervertebral disc replacement and/or spinal fusion. The tool, i.e. device, allows a spinal surgeon to more easily access and position a replacement disc or graft within the vertebral space. In some embodiments, the device allows a spinal surgeon to control implantation depth of a replacement disc or graft. Additionally disclosed is a multifunctional device that permits substantially single-handed operation. Such a device reduces the number of tools required for performing multiple functions during disc replacement surgery and/or spinal fusion surgery, while freeing up an operator's other hand. In some embodiments, the tool, i.e. device, is rotatable about an axis extending between a pair of opposed arms. Such embodiments provide improved ergonomics and ease of use during the disc replacement surgery and/or spinal fusion surgery. By providing one or more of the preceding advantages, the device described herein improves the ease and speed with which disc replacement or spinal fusion surgery can be completed using an anterior lumbar approach. The terms "vertebral distractor-inserter," "distractor-inserter," and "device" are interchangeable as used herein.

The invention will now be further described with reference to the appended drawings, which are intended to be illustrative of certain preferred embodiments of the invention, but are not intended to limit the scope of the invention. One of skill in the art will recognize that other embodiments of the invention are possible within the scope of the invention; and no disclaimer of such additional embodiments is intended by referring to the illustrative examples.

Figure 1A:
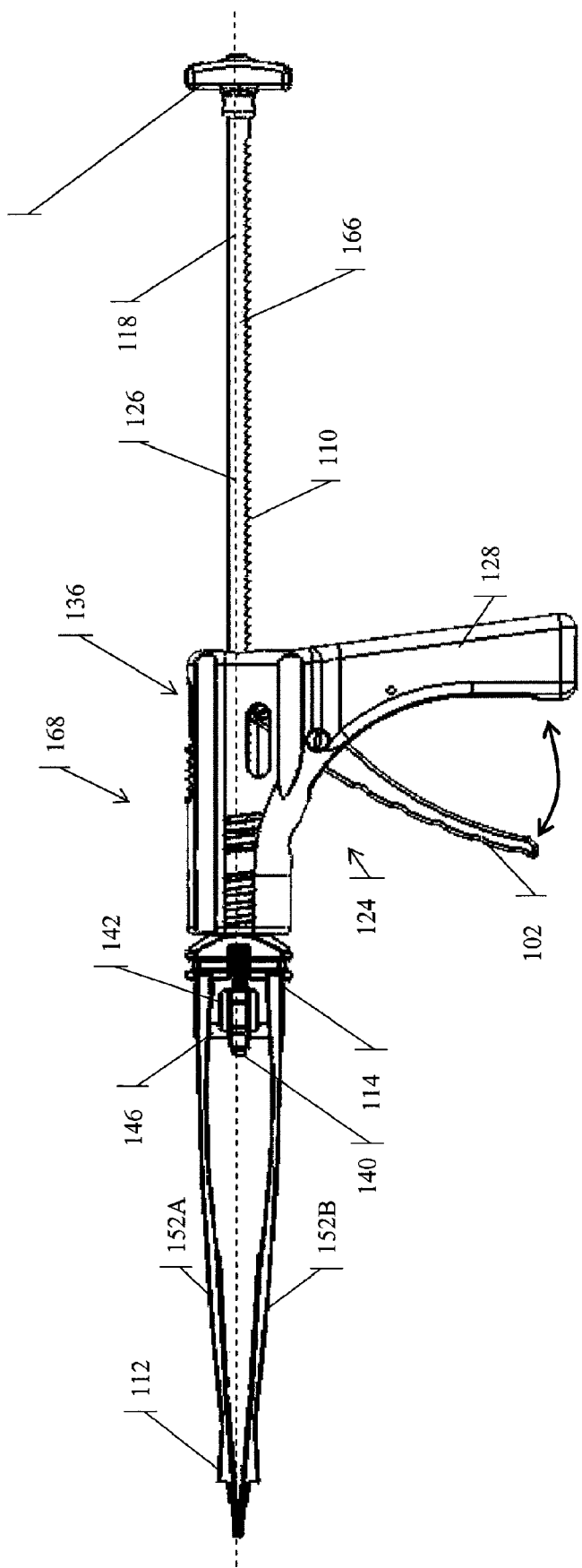

FIGS. 1A, 1B, and 1C depict external views of one currently preferred embodiment of the device 168. FIG. 1A depicts an embodiment of a vertebral distractor-inserter 168 comprising a housing 136, a pair of opposing arms 152A, 152B in mechanical communication with the housing 136, a driving rod 126 extending through at least a portion of the housing 136 and between the pair of opposing arms 152A, 152B, wherein the driving rod 126 comprises an axis 118 and a surface 166 with a plurality of angled ratchet teeth 110 on at least a portion of the surface 166, and a ratchet drive mechanism in mechanical communication with the driving rod 126. In some embodiments, the vertebral distractor-inserter 168 comprises a handle 128 attached to the housing 136. In some embodiments, the vertebral distractor-inserter 168 does not comprise a housing 136. In some embodiments, the housing 136 does not enclose the rod 126. In some embodiments, the rod 126 is external to, but in communication with, the housing 136.

FIG. 1A further depicts an embodiment having an activating lever 102, which is in mechanical communication with the driving rod 126. Movement of the activating lever 102 in the direction of the handle 128 causes the driving rod 126 and an implant (not shown) at the distal end of the driving rod 126 to move distally relative to the housing 136. The mechanical communication may be effected through a number of means; in the depicted embodiment the mechanical communication is through a ratcheting drive mechanism 124 within the housing 136. The ratcheting drive mechanism 124 uses ratchet teeth 110 to grip the driving rod 126 and drive the implant and the rod 126 distally when the activating lever 102 is moved toward the handle 128.

The embodiment shown has an implant coupler 140 and an implant depth adjustor 142. The implant coupler 140 abuts the implant and transfers force from the driving rod 126 to the implant, which in turn forces the lower arm 15213 and the upper arm 152A apart, providing distracting force. The implant depth adjustor controls the depth to which an implant can be implanted when the depth stop 146 contacts the vertebra (not shown) during insertion. The embodiment has an arm depth guard 112, which determines the maximum depth to which the arms 152A, 152B can be inserted between the vertebrae during distraction. In the embodiment shown in FIG. 1A, the driving rod 126 is fully retracted and the distal end of the arms 152A, 152B are ready for insertion between the vertebrae for subsequent distraction and implant insertion.

FIG. 1B shows a similar embodiment of the device 168 in the fully extended position, wherein the implant coupler 140, depth stop 146 and depth adjustor 142 are at their most distal position. This view shows what the device 168 would look like after use of the device 168 to distract the vertebrae and after insertion of the implant. This figure also shows an arm pivot 114, about which the arms 152A, 152B may pivot to distract the vertebrae upon distal movement of the implant and the implant coupler 140, the implant depth adjustor 142, and the implant depth stop 146.

FIG. 1C depicts a top view of an embodiment of the device 168 with the implant coupler 140, depth stop 146, and adjustor 142 in an intermediate position between full retraction and full extension. In this view, the housing 136 is shown along with the driving rod 126, which extends through the housing 136. Also visible is the implant depth stop 146, which travels in a groove 182 of the arm 152A. This view also shows a knob 150 on the proximal end of the driving rod 126, discussed further below.

Figure 2A:
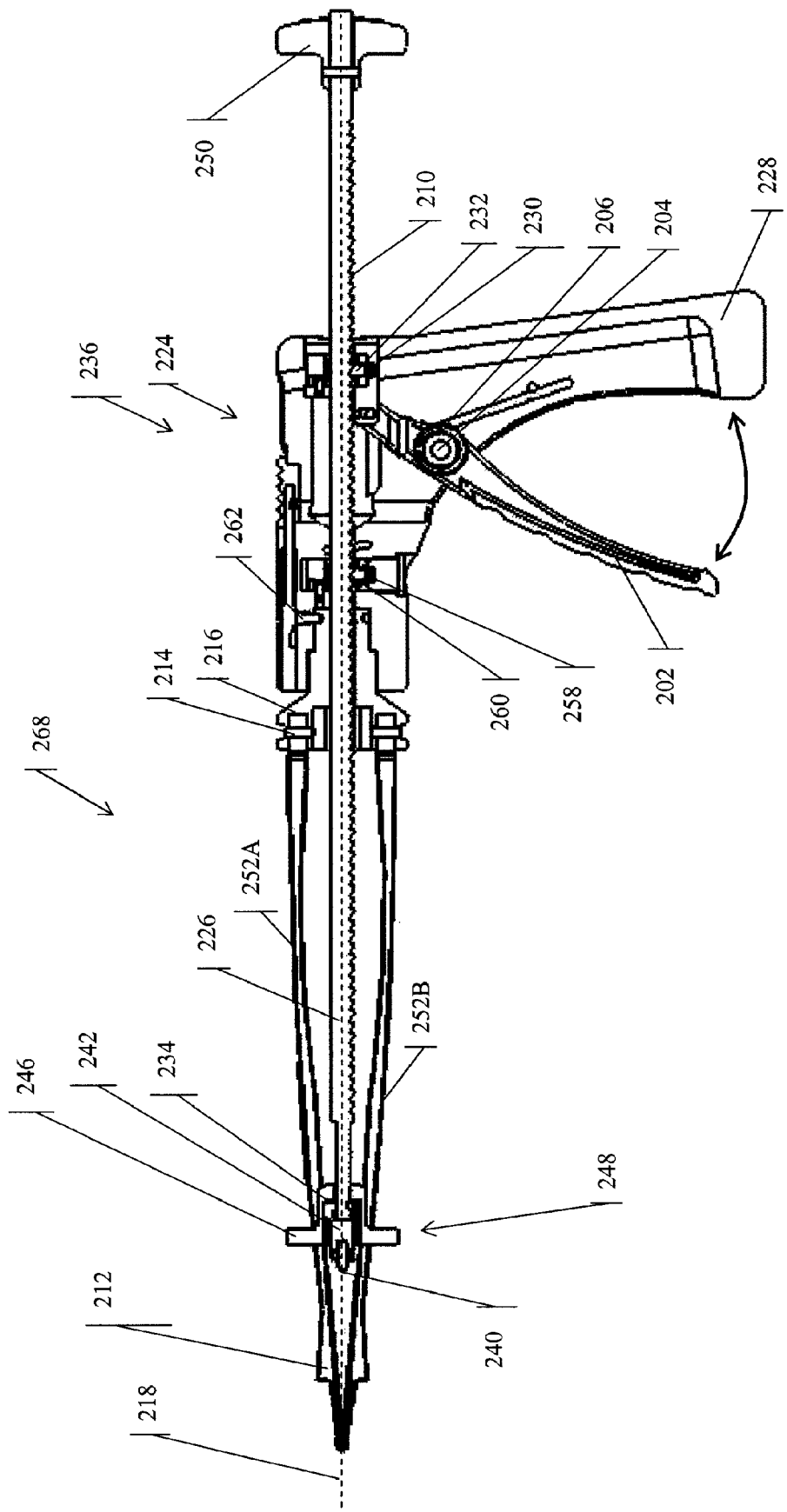
FIG. 2A: Shows a cutaway side view of an embodiment of the device having ratchet teeth engaged.

FIG. 2A shows a cutaway side view of an embodiment of the device 268 having ratchet teeth 210 engaged. Further shown is a first ratchet pawl 232 and a first pawl spring 230 which work together with the activating lever 202, activating lever spring 206 and activating lever pivot 204 to drive the driving rod 226 distally when the activating lever 202 is moved toward the handle 228 (i.e. toward a second position from a first position, shown by the double-headed arrow of FIG. 2A). When an operator grips the handle and the activating lever 202 in one hand and pulls the activating lever 202 proximally toward the handle 228, the activating lever 202 moves the first ratchet pawl 232 distally by pivoting about the activating lever pivot 204. Since the first ratchet pawl 232 is engaged against the ratchet teeth 210 of the driving rod 226, the distal motion of the ratchet pawl 232 drives the driving rod 226 distally. Also depicted in this view is a second ratchet pawl 260 and a second pawl spring 258. The second ratchet pawl 260 cannot move distally or proximally, but the second ratchet spring 258 allows the second pawl to move away from the driving rod 226 as each angled ratchet tooth 210 advances distally. Once each tooth 210 passes the second pawl 260, the pawl spring 258 pushes the second pawl 260 back toward the driving rod 226, to engage the next ratchet tooth 210 along the driving rod 226. Thus the second ratchet pawl 260 allows distal motion of the arm 226 and prevents proximal motion of the arm 226. As the activating lever 202 is pulled again or farther toward the handle 228, further distal motion is imparted to the arm 226.

Thus, the second ratchet pawl 260 and the second pawl spring 258 cooperate to restrict or oppose proximal motion of the driving rod 226 as the activating lever 202 is reset away from the handle 228. In the depicted embodiment, the activating lever 202 has a spring 206 which biases the lever 202 toward the first position. Once the operator releases the force on the lever 202, the activating lever spring 206 moves the lever 202 away from the handle 228 toward its original position. As this occurs, the first pawl 232 and first pawl spring 230, linked to the activating lever 202, are also returned toward their original positions relative to the housing 236 prior to the operator pulling the lever 202 proximally. This occurs with no distal or proximal motion of the driving rod 226 since the first pawl spring 230 allows the first pawl 232 to move away and toward the driving rod 226 along the ratchet teeth 210 of the rod 226 as the pawl 232 ramps along the teeth 210 proximally. The second ratchet pawl 260, engaged against the ratchet teeth 210, opposes proximal motion of the rod 226 during this action. In embodiments where a gripping or other type of driving mechanism is used, the second ratcheting pawl 260 and spring 258 may be used to provide similar restricted proximal motion where the driving rod 226 comprises some ratchet teeth 210 on at least a portion of the rod 226 which can cooperate with the second ratchet pawl 260 and spring 258.

It is to be understood that the spring 206 may be eliminated in some embodiments and still provide substantially single handed operation. In such cases, the activating lever 202 will have to be moved toward the first position manually. This can be facilitated by including a closed handle (loop) similar to those common on scissors and forceps at the lower end of the activating lever 202, through which an operator may place her fingers and by means of which an operator can impart force to the lever 202 in either the direction away from or toward the handle 228 with a single hand.

In another embodiment, the device comprises a holding means wherein a second ratchet pawl and second ratchet spring are not present. The holding means instead may comprise, for example, a pneumatic grip, a hook, a latch, a grabbing device, the gripping mechanism described further herein, manually holding the driving rod in its distal position, or another mechanical means of restricting proximal motion.

In other embodiments, the device comprises a driving means comprising a first ratchet pawl and a spring that engages a thread which winds around the driving rod. Ratchet teeth may be unnecessary in this embodiment. The activating lever may instead drive the driving rod and implant distally by engaging the threads in the same ratcheting manner described herein, and retraction may be achieved by rotating the driving rod such that the rod moves proximally with the ratchet pawls engaged against the threads of the rod.

In other embodiments, the device comprises a driving means comprising for example, a pneumatic grip, a hook, a latch, a grabbing device, the gripping mechanism described further herein, an element adapted and configured for manually pushing the driving rod distally, or another mechanical means of moving the rod and the implant distally to distract the arms and insert the implant. These and similar embodiments will be apparent to the person skilled in the art upon consideration of alternative embodiments described herein.

Further depicted in FIG. 2A is an implant interface 248, an implant depth stop 246, an implant depth adjustor 242, and an implant coupler 240 all of which are adapted and configured to cooperate with the arms 252A, 252B and the driving rod 226 and the implant to drive the implant distally, to distract the vertebrae, and to place the implant within the intervertebral space at a controlled depth. Also shown is the arm pivot 214 and the arm spring 216, which allow outward motion of the arms 252A, 252B away from the axis 218 of the driving rod 226 as the implant and implant interface 248 are driven distally. Further depicted in this figure is a first rotation element 234 and second rotation element 262, which together allow the handle 228 and the driving rod 226 to rotate relative to the arms 252A, 252B, the implant interface 248, and the implant.

In some embodiments, the vertebral distractor-inserter 268 comprises a ratchet drive mechanism 224, which comprises an activating lever 202 mounted to the housing 236 by an activating lever pivot 204, a first ratchet pawl 232 coupled to the activating lever 202 and adapted to engage the ratchet teeth 210 and move the driving rod 226 distally relative to the housing 236, and an engaging element to oppose proximal motion of the driving rod relative to the housing. The engaging element can be, for example, a gripping element 470 as shown in FIG. 4, a grabbing element, a hooking element, a pressurized holding element; or it can be a manual pushing or holding element.

In some embodiments the ratchet drive mechanism 224 comprises an activating lever spring 206 coupled to the activating lever 202 and the handle 228, wherein the activating lever spring 206 opposes proximal movement of the lever 202 relative to the handle 228. In some embodiments of the distractor-inserter 268, the ratchet drive mechanism 224 comprises a first pawl spring 230 that opposes downward movement of the first pawl 232 and a second pawl spring 258 that opposes downward movement of the second pawl 260.

In some embodiments of the distractor-inserter 268, the driving rod 226 comprises a distal end and an implant interface 248 coupled to the distal end of the driving rod 226. In some embodiments, the distractor-inserter 268 comprises an implant in contact with the implant interface 248, whereby distal motion of the driving rod 226 imparts distal motion to the implant through the implant interface 248; and distal motion of the implant in turn forces the opposing arms 252A, 252B apart.

In some embodiments, each opposing arm 252A, 252B comprises an arm pivot 214. Some embodiments comprise a pair of opposing arms 252A, 252B comprising an arm spring 216. Some embodiments comprise an opposing arm 252A, 252B comprising an arm depth guard 212. In some embodiments, the implant interface 248 comprises an implant coupler 240.

Figure 2B:
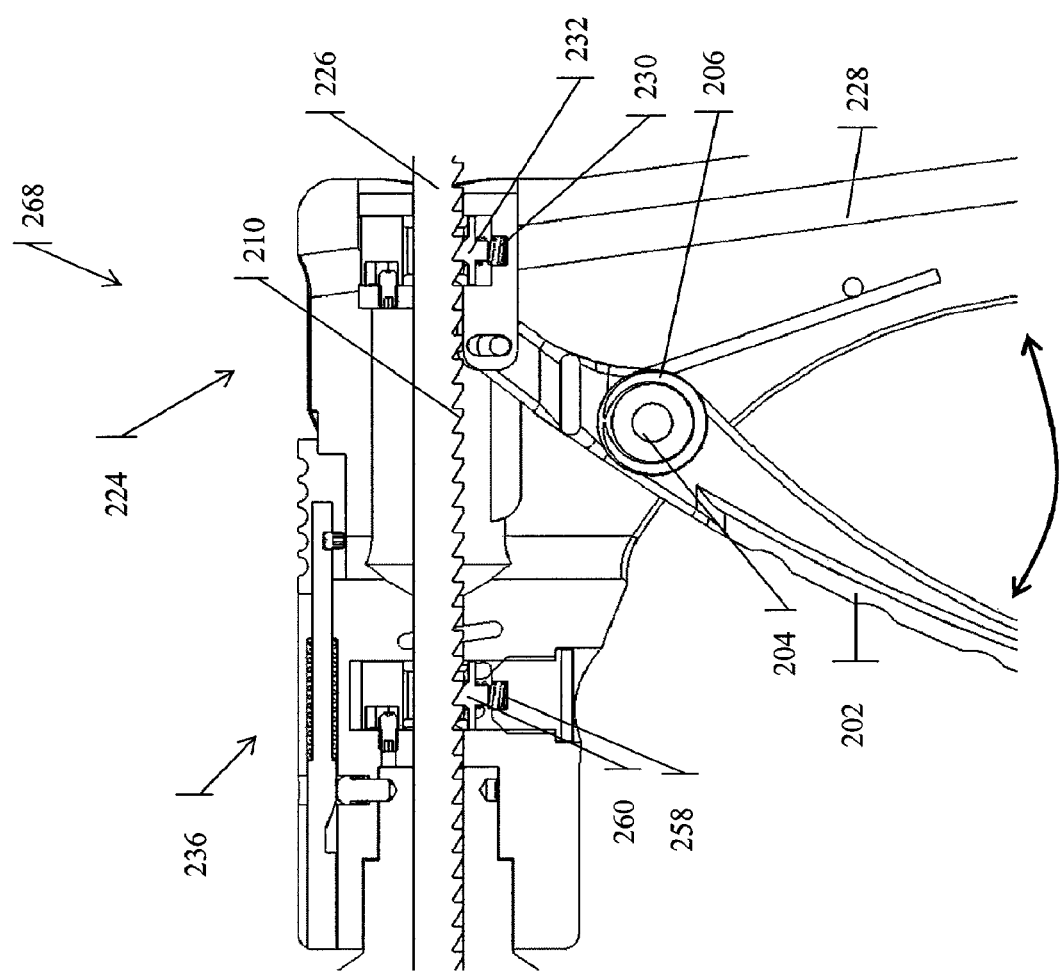
FIG. 2B: Shows a cutaway side view of the housing of an embodiment of the device having ratchet teeth engaged by the drive mechanism wherein the activating lever is in a first position.

FIG. 2B shows a cutaway side view of the housing 236 of an embodiment of the device 268 having ratchet teeth 210 engaged by the drive mechanism 224 wherein the activating lever 202 is in a first position. A first ratchet pawl 232 engages the ratchet teeth 210 of the driving rod 226 and a first pawl spring 230 opposes motion of the first pawl 232 away from the driving rod 226 (downward, in the depicted embodiment, although, it could be in any direction away from the driving rod 226). Also shown is a second ratchet pawl 260. A second pawl spring 258 opposes motion of the second pawl 260 away from the driving rod 226 (downward, in this case, although it could be in any direction away from the driving rod 226). Further depicted is the activating lever pivot 204 about which the activating lever 202 pivots to drive the driving rod 226 and, therefore, the implant distally by engaging and moving the ratchet teeth 210 distally when the activating lever 202 is moved toward the handle 228. Also depicted is the activating lever spring 206, which opposes activating lever 202 movement toward the handle 228, and which is capable of moving the activating lever 202 away from the handle 228 when the activating lever 202 is released.

Figure 2C:
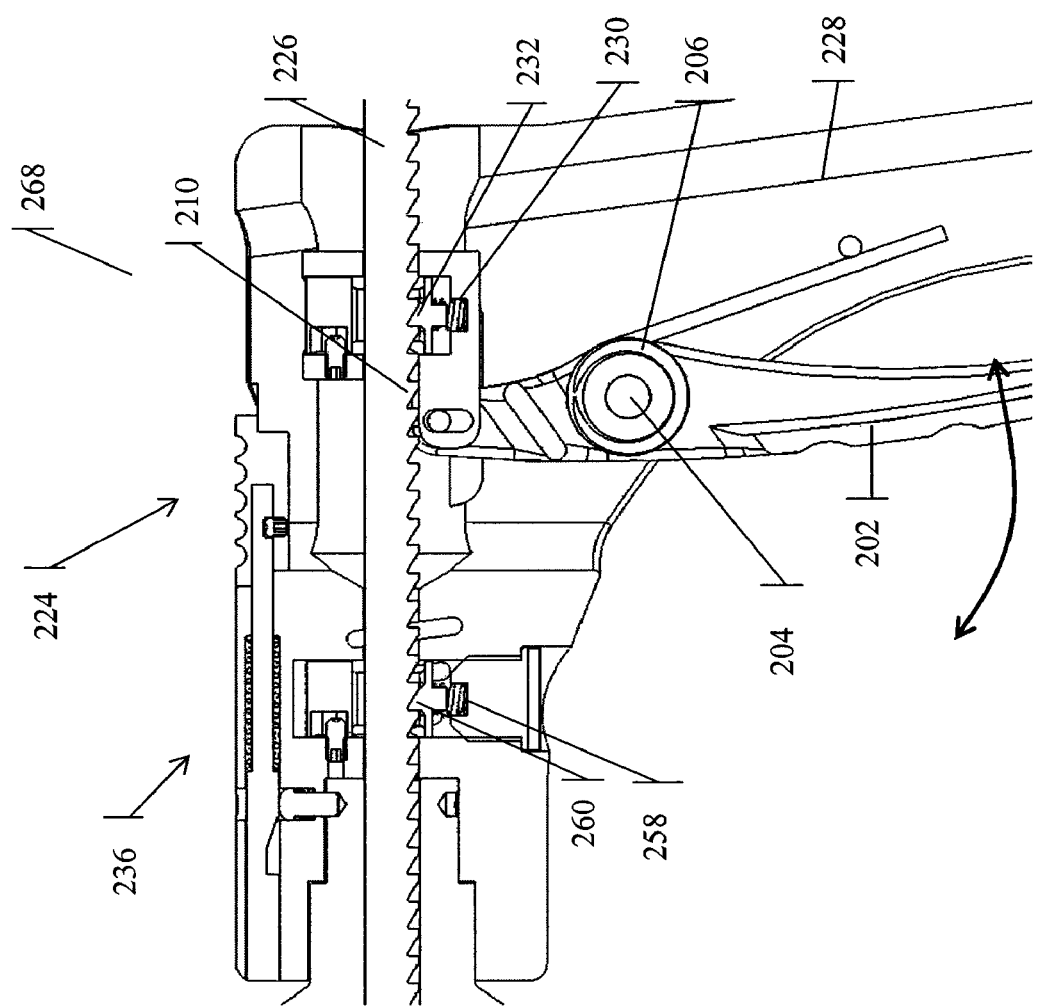
FIG. 2C: Shows a cutaway side view of the housing of an embodiment of the device having ratchet teeth engaged by the drive mechanism wherein the activating lever is in a second position.

FIG. 2C shows a cutaway side view of the housing of an embodiment of the device having ratchet teeth 210 engaged by the drive mechanism 224, wherein the activating lever 202 is in a second position toward the handle 228. The drive mechanism 224, the first ratchet pawl 232, and the driving rod 226 are shown in as they appear when the activating lever 202 is moved toward the handle 228. As can be seen, movement of the activating lever 202 toward the handle 228 causes the first ratchet pawl 232, and the driving rod 226, through engagement of the ratchet pawl 232 with the ratchet teeth 210 of the driving rod 226, to move distally relative to the housing 236.

In some embodiments, the vertebral distractor-inserter 268 is adapted for single-handed use. In such an embodiment, the vertebral distractor-inserter 268 is adapted for substantially single-handed distraction of vertebrae and insertion of a vertebral implant.

It is to be understood in regard to the phrase "single-handed," the functions of holding the device in place and advancing the rod 226 and implant may in most instances be performed with a single hand. However, it is also noted that in some cases, depending upon operator preference and the vagaries of patient physiology, two hands may be used, e.g. to impart greater force to the lever 202, without departing from the spirit and scope of the invention. The phrase "single-handed" thus distinguishes embodiments of the invention over distractor-inserter devices in which the device is held in place with one hand and the implant is advanced distally by twisting or striking an implant arm. It is considered that whether used with one hand or two, the device of the present invention provides force to both distract vertebrae and advance the implant with lessened torque, impact force or other physiologically disruptive forces, and thus less trauma to the patient, than is generally required with previously known devices. In currently preferred embodiments, the device of the present invention also permits the operator to hold the device in place and impart force for distraction and insertion with a single hand. In addition to the aforementioned advantages, single handed use is amenable to less invasive surgery than two-handed use.

Figure 3A:
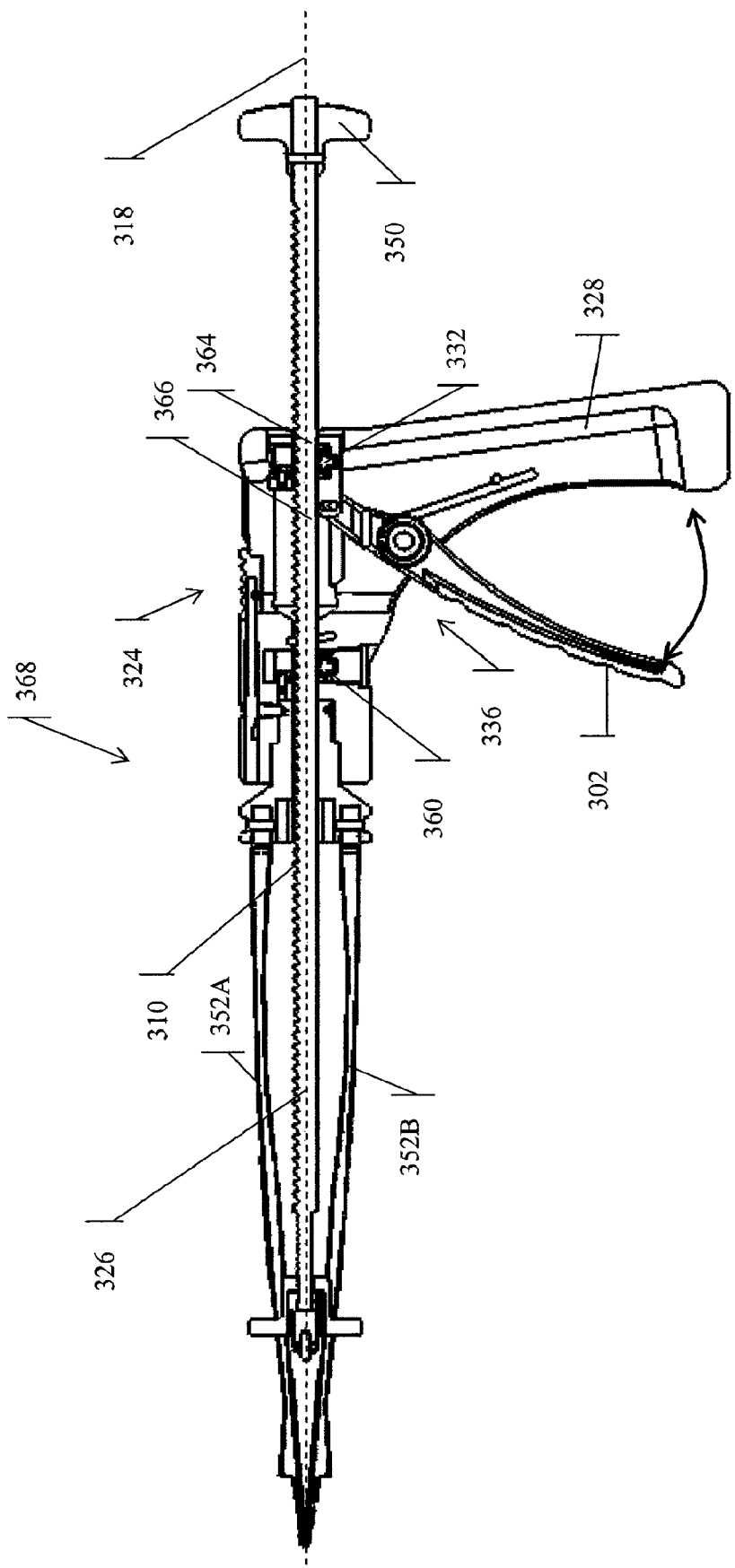
FIG. 3A: Provides a cutaway side view of an embodiment of the device having ratchet teeth disengaged for retraction of the driving rod.

Some embodiments of the device are adapted and configured to allow retraction of the implant interface and the driving rod relative to the arms of the device. This may be achieved in a number of ways. In the embodiment of the device 368 depicted in FIG. 3A, a cutaway side view of the device 368 is shown having ratchet teeth 310 disengaged for retraction of the driving rod 326. The driving rod of this embodiment has a surface 366 comprising a substantially smooth area 364 and ratchet teeth 310. When the knob 350 is turned about the axis 318, preferably with knob 350, such that the ratchet teeth 310 are no longer engaged by the ratchet pawl 332, or the ratchet pawls 332, 360 if there are two, the driving rod 326 is free to be moved proximally (or retracted) relative to the housing 336 and the arms 352. Although this action is favorably carried out by the operator holding the handle 328 in one hand and turning the knob 350 with the other, this action is not to be interpreted as derogating in any way single-handed operation of the device 368, as single-handed operation generally refers to simultaneously holding the handle 328 and imparting drive force to the driving arm 326 with a single hand, and that only in most cases. As the driving rod 326 may be easily disengaged from the pawls 332, 360 with, for example, a single 180° twist about the axis 318, it is considered that the present invention provides for easier and faster retraction of the driving arm 326 than is provided by previously known devices that require screwing the arm backwards.

In another embodiment, the driving rod 326 may comprise a threading around the driving rod instead of ratchet teeth, wherein the ratchet pawl 332 or ratchet pawls 332, 360 if there are two, may engage the threads instead of ratchet teeth. To retract the rod 326, rather than turning the driving rod 326 until the pawl(s) 332, 360 disengages the teeth, and then pulling the rod 326 proximally, the rod 326 and, thereby, the implant interface 248, may be retracted by turning the rod 326 around the long axis of the rod 326. In this embodiment, the rod threads are not disengaged from at least the first ratchet pawl 332.

Other embodiments may comprise combinations of threads, ratchet teeth 310, and/or a substantially smooth area 364 along the driving rod surface 366, and a combination of ratcheting and gripping elements to provide the controlled distal and proximal movement of the driving rod 326, the implant, and implant interface 248 relative to the arms 352A, 352B, and to the housing 336.

Likewise, the embodiment of FIG. 3B shows a cutaway side view the housing 336 of an embodiment of the device 368 having ratchet teeth 310 of the driving rod 326 disengaged from the first ratchet pawl 332 and second ratchet pawl 360 for retraction of the driving rod 326. Also shown is the substantially smooth area 364 of the driving rod 326 surface 366 which allows proximal retraction of the driving rod 326 and, thereby, the implant interface 248.

If needed or desired, retraction of the device 368 using the features and methods described herein may also allow retraction of the implant prior to insertion of the implant between the vertebrae.

In some embodiments, the ratchet teeth 310 extend along the driving rod 326 a length sufficient to allow the arms 352 to touch when the implant is loaded prior to distraction and to allow the implant to be inserted between the vertebrae. In some embodiments, for example, the ratchet teeth 310 extend along the length of the driving rod 326 for between about 6 and about 10 inches, for about 8 inches, for about 12 inches, for about 16 inches, for at least 3 inches, or for the entire length of the rod. In referring to the ratchet teeth length along the rod, "about" refers to variations of 0.5 inches to 1 inch, or of 1 inch to 2 inches.

In some embodiments, the surface 366 of the driving rod 326 comprises an area 364 that is substantially free of ratchet teeth on a contiguous longitudinal surface 366 of the driving rod, and the driving rod 326 is movable proximally relative to the housing 336 upon rotation of the rod 326 about its axis 318 such that the ratchet pawls 332, 360 are in contact with the contiguous longitudinal surface 364 that is free of ratchet teeth. In some embodiments, the ratchet teeth 310 disengage from first and second ratchet pawls 332, 360 upon rotation of the driving rod 326 about its axis 318. In some embodiments, the driving rod 326 comprises a proximal end having a knob 350.

Figure 4A:
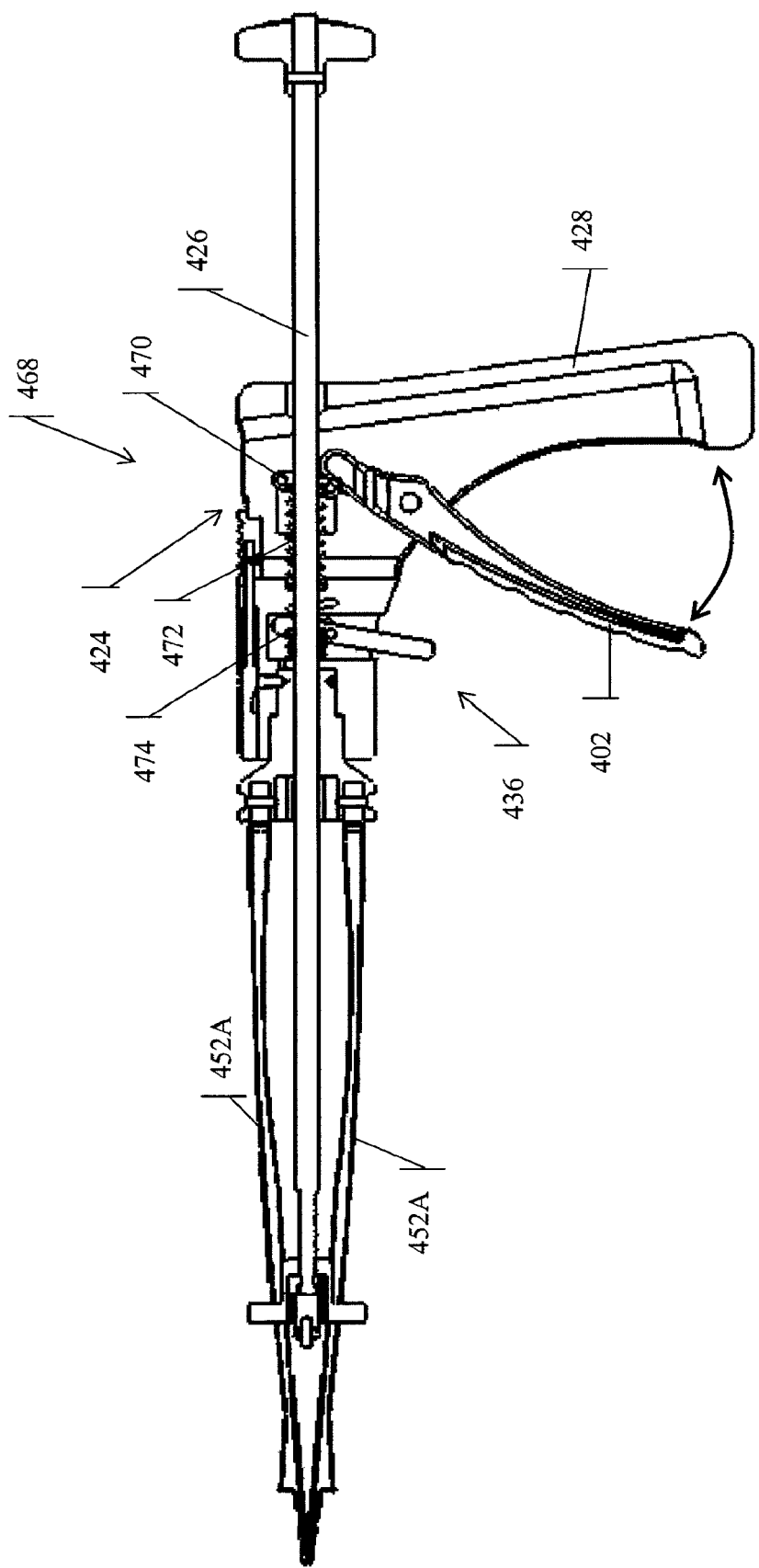
FIG. 4A: Depicts a non-ratcheting embodiment of the device.

FIG. 4A shows a non-ratcheting embodiment of the device 468. The device 468 has a pair of opposing arms 452A, 452B and two gripping elements 470, 474, wherein the first gripping element 470 is adapted and configured to grip and drive the driving rod 426 distally when the activating lever 402 is moved toward the handle 428. The second gripping element 474 allows distal movement of the driving rod 426, but opposes proximal motion of the driving rod 426 when the activating lever 402 is released and allowed to move away from the handle 428, for example, to its original resting (first) position. The first gripping element 470 also releases its grip on the driving rod 426 when the lever 402 is moved away from the handle 428, for example, to its original resting position. The first gripping spring 472 moves the first gripping element 470 proximally when the activating lever 402 is released. The first gripping element 470 is adapted and configured to only grip the driving rod 426 upon driving rod distal motion. Similarly, in the embodiment of FIG. 4, the second gripping element 474 is adapted and configured to only grip the driving rod 426 upon driving rod proximal motion.

Figure 4B:
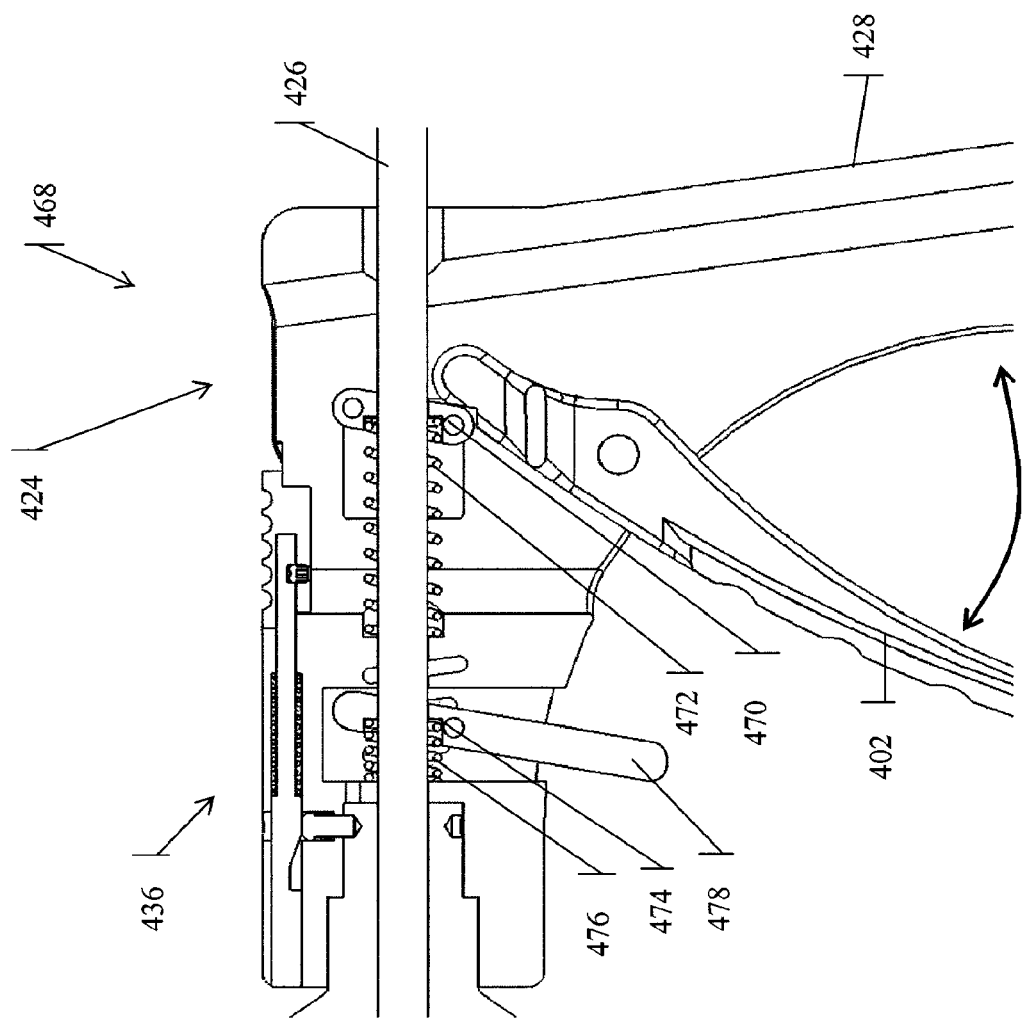
FIG. 4B: Shows a cutaway side view of the housing of a non-ratcheting embodiment of the device.

FIG. 4B shows a cutaway side view of the housing 436 of a non-ratcheting embodiment of the device 468. The first gripping spring 472 opposes the distal motion of the first gripping element 470 and the driving rod 426 that an operator causes by moving the activating lever 402 toward the handle 428. A second gripping spring 476 opposes proximal motion of the driving rod 426 when the lever 402 moves away from the handle 428. Movement of the lever 402 away from the handle 428 may be manually forced, or may be the result of an activating lever spring 206 within the handle 428 and attached to the activating lever pivot 204 which opposes movement of the lever 402 toward the handle 428. Also depicted is a gripping release lever 478, which is adapted to permit release the second gripping member 474 to allow the driving rod 426 to be retracted.

Some embodiments comprise a drive mechanism 424 comprising at least one gripping element 470 which opposes proximal motion of the drive mechanism 412. Activating the lever 402 drives the implant distally by moving the driving rod 426. As the activating lever 402 returns to its original position, the first gripping element 470 releases the driving rod, however the second gripping element 474 opposes proximal motion of the driving rod 426 and the implant. The drive mechanism may comprise a gripping spring, 472, or 476, or two gripping springs 472 and 476.

In some embodiments of the distractor-inserter 468, the drive mechanism 424 comprises a gripping element 474 and a ratcheting drive mechanism as described previously. Some embodiments comprise other means for driving implant distally. These means can be other mechanical mechanisms capable of allowing unidirectional movement, along with a release mechanism for reversing such unidirectional movement. Some embodiments comprise other means for distracting the arms. The means for distracting may be other tools altogether through which the distractor-inserter may be placed and used to place the implant.

FIGS. 5A & 5B depict views of an embodiment of the device 568 showing relative rotation of the arms 552A, 552B and the handle 528. Also shown in these views are at least one arm depth guard 512 and the activating lever 502. In use, the patient is stationary, and thus the arms 552A, 552B of the device 568 and the implant must remain in a fixed position relative to the patient during distraction and insertion for patient safety and for optimal implantation results. However, the user of the device 568 may need to be at a variety of angles relative to the patient; thus, the device is adapted to allow distraction and insertion in a more ergonomic manner for the user and, thus, a safer manner for the patient. This is achieved by allowing at least one degree of freedom of rotation in the device 568. That is, the device 568 is adapted to allow rotation of the handle 528, activating lever 502, and housing 536 relative to the arms 552A, 552B and the implant, about the axis 218 of the driving rod 226. This is achieved by providing at least one rotation element 234 (not shown in FIG. 5, shown in FIG. 2A) that allows free rotation of these elements relative to each other.

FIG. 5A shows the axial view of the device 568 looking from the distal end to the proximal end of the device 568. In this view, the arms 552A, 552B are in a neutral position relative to the housing 536. In FIG. 5B, also an axial view of the device 568 looking from the distal end to the proximal end of the device 568, the arms 552A, 552B are rotated relative to the housing 536 about the driving rod axis 218. While it may appear that the arms 552A, 552B are rotated, in use the rotation is relative, and the user will more likely rotate the housing 536 and the activating lever 502 relative to the arms 552A, 552B, keeping the arms 552A, 552B and implant aligned appropriately with the vertebral anatomy of the patient.

In some embodiments, a vertebral distractor-inserter 568 comprises a pair of opposing arms 552A, 552B, a housing 536 in mechanical communication with the pair of opposing arms 552A, 552B and rotatable about an axis 218 extending between the opposing arms 552A, 552B, and a driving rod 226 extending through at least a portion of the housing 536 and between the pair of opposing arms 552A, 552B. Some embodiments comprise a distal end having an implant interface 248, wherein the housing 536 and at least a portion of the driving rod 226 are rotatable relative to the pair of opposing arms 552A, 552B and the implant interface 248. Some embodiments further comprise an implant interface 248 comprising an interface rotation element 262, whereby the interface rotation element allows rod 226 rotation relative to the pair of opposing arms 552A, 552B. Some embodiments further comprise a housing 536 comprising a housing rotation element 234, whereby the housing rotation element 234 allows housing 536 and rod 226 rotation relative to the pair of opposing arms 552A, 552B.

In some embodiments, a vertebral distractor-inserter 568 comprises a pair of opposing arms 552A, 552B, a housing 536 in mechanical communication with the pair of opposing arms 552A, 552B and rotatable about an axis 218 extending between the opposing arms 552A, 552B, a driving rod 226 extending through at least a portion of the housing 536 and between the pair of opposing arms 552A, 552B, and a drive mechanism 224 adapted to move the driving rod 226 distally relative to the housing 536.

In some embodiments of a rotatable vertebral distractor-inserter 536, the vertebral distractor-inserter comprises a drive mechanism 224. Embodiments of the drive mechanism are described herein.

Figure 6A:
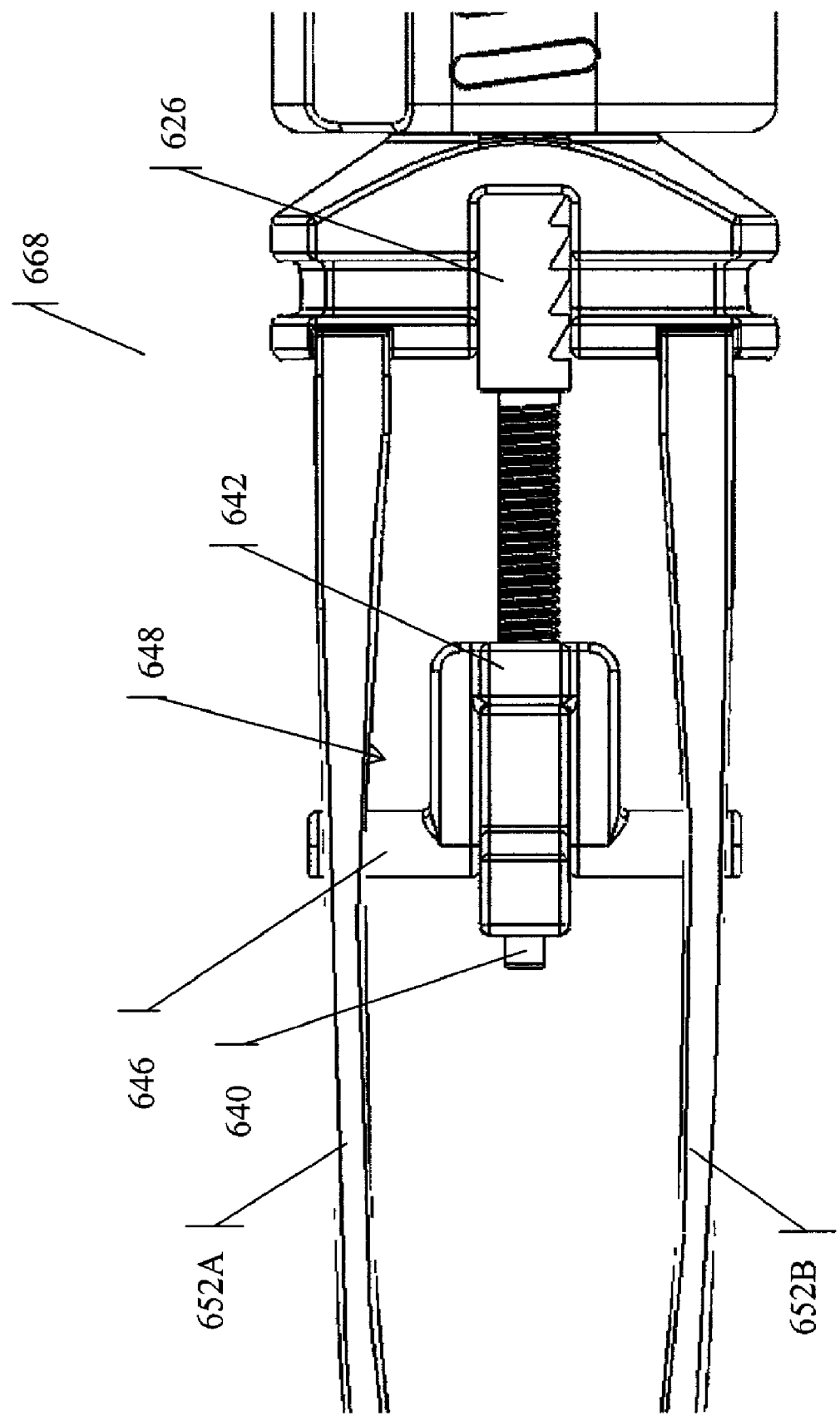
FIGS. 6A & 6B: Depict views of an embodiment of the device showing an implant depth adjustment feature.
Figure 6B:
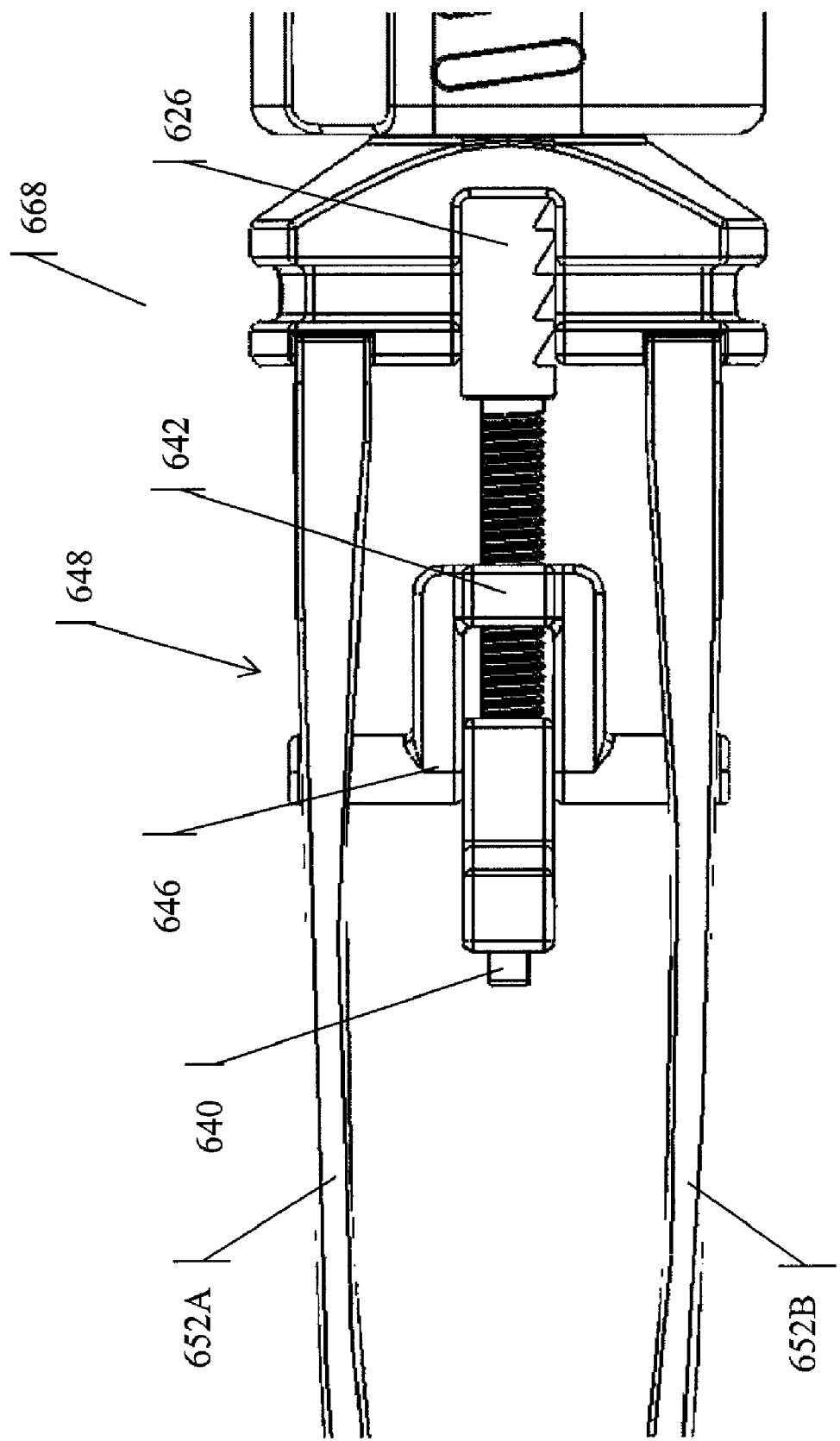

FIGS. 6A & 6B depict views of an embodiment of the device 668 having an implant depth adjustment feature. FIG. 6A shows a depth adjustor 642 at its distal-most setting, which results in the implant moving beyond the distal end of the arms 652A, 652B the least distance. When the implant depth adjustor 642 is moved proximally, moving the depth stop 646 distally relative to the implant or the implant coupler 640, or both, an implant at the distal end of the implant interface 648 can move farther distally into the space between the vertebrae because the depth stop 646 is more proximal than when the adjustor 642 is at its distal-most setting. FIG. 6B shows an intermediate setting for the implant depth adjustor 642, wherein the implant can move more distally relative to the distal end of the arms 652A, 652B than the implant can when the adjustor 642 is at its distal-most setting, as is depicted in FIG. 6A. The implant depth adjustor 642 can be threaded proximally and distally to move the implant depth stop 646 and control, thereby, the distal depth achievable by the implant using the device 668. Other mechanisms for adjusting this depth are possible including, for example, a ratchet, a peg, a clamp, and a grip. In some embodiments, the implant depth stop 646 will be adjusted before placing the distal ends of the arms 452A, 452B into the intervertebral space and will remain in the same position throughout the procedure. The operator may pre-determine the implant depth in any art-recognized means, e.g. by measuring the depth with various imaging techniques or, after the vertebrae have been accessed, by in situ measurement methods. Since adjustment of the implant depth generally occurs before the device is inserted into the patient, such adjustment does not derogate the single-handed use of the device, as explained with reference to other steps ancillary to distraction and insertion, above.

In some embodiments, the invention provides a vertebral distractor-inserter 668 comprising a housing 136, a pair of opposing arms 652A, 652B in mechanical communication with the housing 136, a driving rod 626 extending through at least a portion of the housing 136 and between the pair of opposing arms 652A, 652B, a drive mechanism 224 adapted to move the driving rod 626 distally relative to the housing 136, and an implant depth adjustor 642 that is adjustable to a plurality of implant depth settings and is adapted to push the distractor-inserter 668 proximally upon insertion of an implant to a selected implant depth setting. The implant depth adjustor 642 may optionally comprise an implant depth stop 646. Example drive mechanisms are previously described herein. This vertebral distractor-inserter 668 may be ratcheting, gripping, a combination of these, or of another type altogether. Any distractor-inserter described herein may be adapted for single-handed use. It may also or alternatively comprise an implant interface 648 as described herein. It may also be adapted such that the housing 136 and at least a portion of the driving rod 626 are rotatable about an axis 118 extending between the opposing arms 652A, 652B, as described herein.

Figure 7:
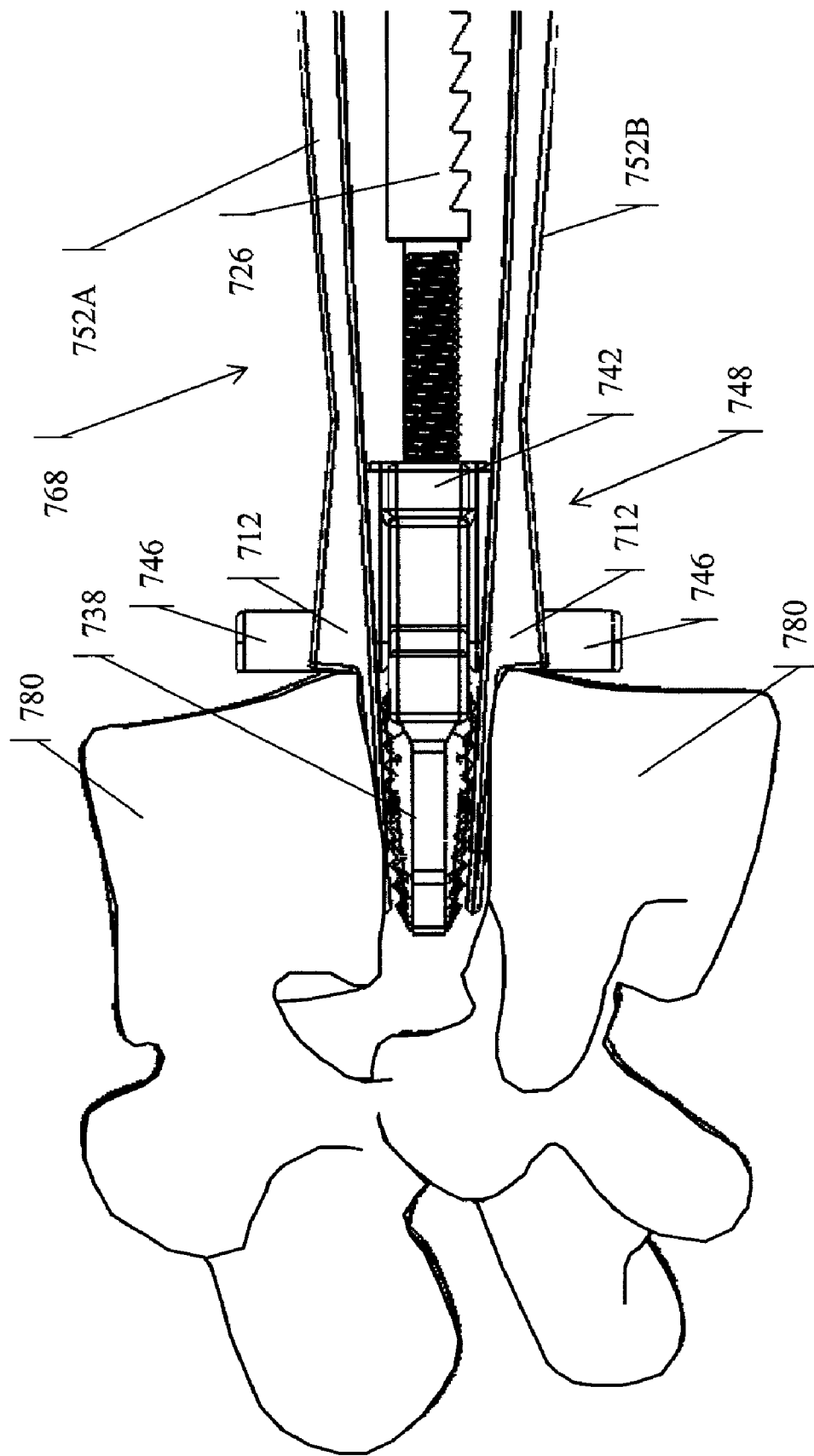
FIG. 7: Shows a view of an embodiment of the device in use. In this view, the vertebrae are distracted to permit insertion of an implant.
Figure 8:
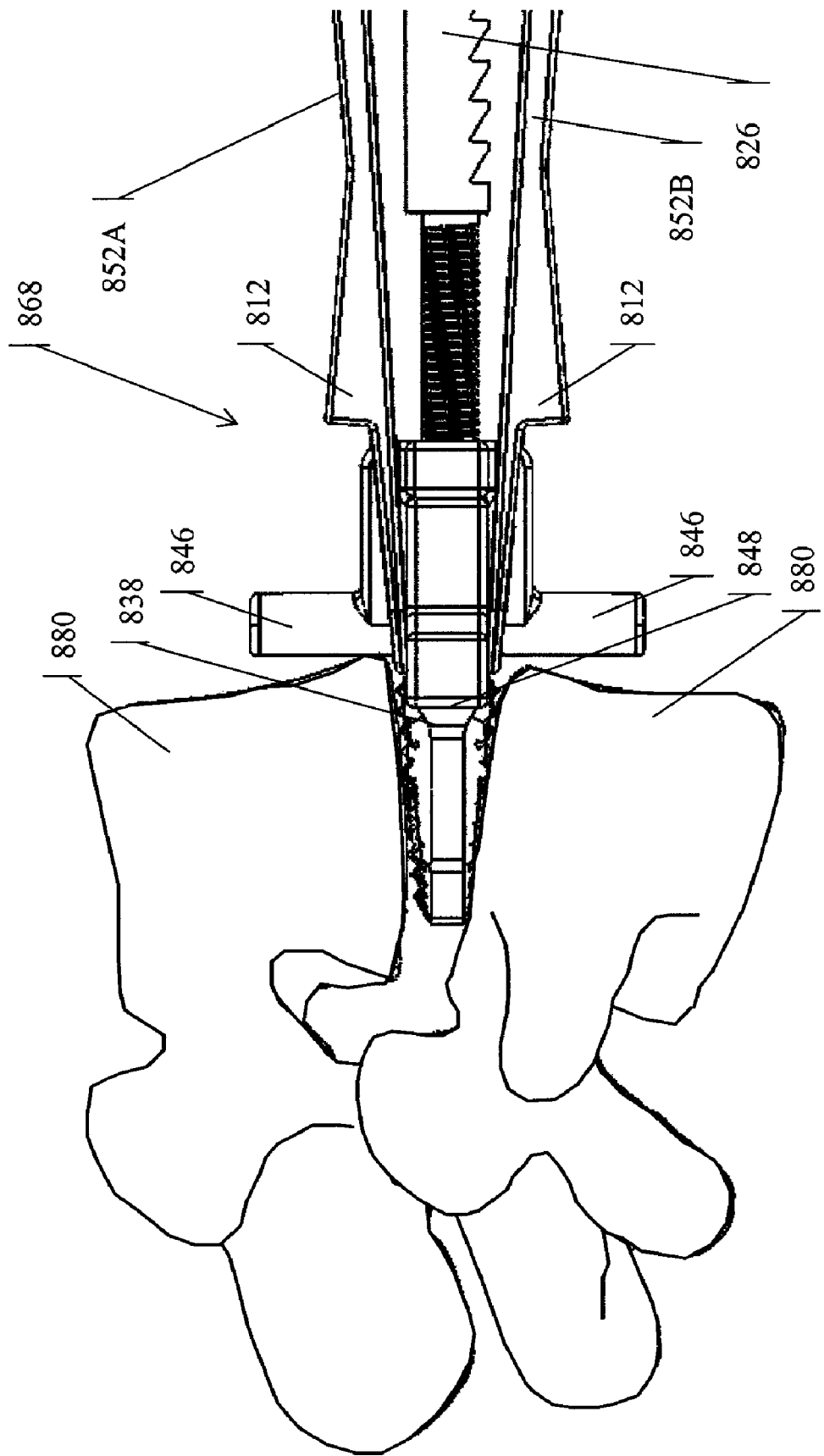
FIG. 8: Shows a view of an embodiment of the device in use. In this view, an intervertebral implant is inserted between the distracted vertebrae, wherein the arms have been retracted from the space between the vertebrae.

FIG. 7 depicts a view of an embodiment of the device 768 in use showing distraction of adjacent vertebrae 780. Shown is the distal end of a device 768 having opposing arms 752A, 752B, arm depth guards 712, a driving rod 726 having an implant interface 748 having an implant depth adjustor 742 and an implant depth stop 746 at the driving rod 726 distal end. Also shown is an implant 738 at the distal end of the implant interface 748 which has distracted the arms 752A, 752B and is positioned between the vertebrae 780. As the driving rod 726 is moved distally relative to the arms 752A, 752B, the arms 752A, 752B will be urged proximally out of the space between the vertebrae 780; but the implant 738 will remain between the vertebrae 780. FIG. 8 depicts a view of an embodiment of the device 868 in use showing insertion of an implant 838 between distracted vertebrae 880 wherein the arms 852A, 852B and the arm depth guards 812 of the arms 852A, 852B have been urged proximally out of the space between the vertebrae 880, and the implant 838 is in direct contact with and sits between the vertebrae 880. The implant 880 cannot move distally when the implant depth stop 846 abuts the vertebra 880.

Multiple elements may be combined in the devices contemplated herein. Additionally, in some embodiments, the invention provides a method for distracting adjacent vertebrae 880 and inserting an implant 838 between the distracted vertebrae 880. The method comprises mounting the implant 838 to a driving rod 826 of a vertebral distractor-inserter device 868 described herein. The device 868 may having a housing 136, a pair of opposing arms 152A, 152B in mechanical communication with the housing 136 having a distal end, and a drive mechanism 224 in mechanical communication with the driving rod 826. The driving rod 826 extends through at least a portion of the housing 136 and between the pair of opposing arms 852A, 852B. The method may further comprise positioning the distal end of the pair of arms 852A, 852B between the vertebrae 880, distracting the vertebrae 880 by single-handed operation of the vertebral distractor-inserter 868, inserting the implant 838 between the distracted vertebrae 880 by single-handed operation of the vertebral distractor-inserter 868, and retracting the pair of opposing arms 852A, 852B from between the vertebrae 880.

In some embodiments, the invention provides a method for distracting adjacent vertebrae 880 and inserting an implant 838 between the distracted vertebrae 880, wherein the distracting step comprises activating the drive mechanism 224 using one hand. The step of activating moves the implant 880 distally and distracts the pair of opposing arms 852A, 852B. In some embodiments of the method, the inserting comprises advancing the implant 880 into the distracted space between the vertebrae 880. In some embodiments of the method, advancing the implant comprises activating the drive mechanism 224 using one hand and extending the implant 880 beyond the distal end of the pair of opposing arms 852A, 852B. In some embodiments, the method comprises the additional step of releasing the implant 880 from the distractor-inserter 868.

In some embodiments of the method for distracting adjacent vertebrae 880 and inserting an implant 838 between the distracted vertebrae 880 the positioning step comprises urging the pair of arms 852A, 852B between the vertebrae 880 up to the position where a depth guard 812 of the arms 852A, 852B contacts the vertebrae 880. In some embodiments, the positioning step comprises urging the pair of arms 852A, 852B between the vertebrae 880 up to a distal depth of at most 75 mm, or at least about 25 mm, or between about 35 mm and 55 mm. When referring to distal depth herein, "about" refers to variations in depth of between 1 mm and 2 mm, or between 2 mm and 5 mm. In some embodiments, the distal depth is the distance from the depth guard 812 to the distal end of the pair of opposing arms 852A, 852B. In some embodiments, the arms 852A, 852B are inserted between the vertebrae 880 up to a distal depth such that the depth guard 812 is proximal to, but not abutting, the proximal side of the vertebrae 880. In some embodiments, the depth guard 812 is proximal to and abutting, or contacting, the proximal side of the vertebrae 880.

In some embodiments, mounting the implant comprises the step of adjusting the implant depth adjustor 642 to control the maximum distal implant depth achievable during the inserting step. In a related embodiment, the implant depth achievable is a maximum of about 25 mm, a minimum of about 0 mm, or between about 3 mm and 8 mm. When referring to implant herein, "about" refers to variations in depth of between 1 mm and 2 mm, or between 2 mm and 5 mm. The implant depth is measured from the distal end of the depth stop 646 to the distal end of the implant interface 648.

In some embodiments, insertion of the implant comprises the step of retracting the pair of opposing arms 852A, 852B from between the vertebrae 880 by abutting the implant depth adjustor 642 against a proximal side of the vertebrae 880 and activating the drive mechanism 224 using one hand.

In some embodiments, the invention provides a method comprising activating the drive mechanism 224 wherein the activating comprises the step of ratcheting the driving rod 826 distally, wherein the driving rod 826 comprises an axis 218 and a surface 366 with a plurality of angled ratchet teeth 210 on at least a portion of the surface 366. In such an embodiment, the drive mechanism 224 may comprise an activating lever 202 capable of movement between a first position and a second position and mounted to the housing 236 by an activating lever pivot 204. The drive mechanism may further comprise a first ratchet pawl 232 coupled to the activating lever 202 and adapted to engage the ratchet teeth 210. The first ratchet pawl may move the driving rod 826 distally relative to the housing 236 as described herein. The drive mechanism may further comprise a second ratchet pawl 260 adapted to engage the ratchet teeth 210 and oppose proximal motion of the driving rod 826 relative to the housing 236 as described herein.

In some embodiments, the invention provides a method comprising gripping the rod 424 and moving the driving rod 424 distally wherein the distractor-inserter is an embodiment as described herein. In some embodiments, the step of ratcheting comprises the step of applying a force to the activating lever 402 to move the lever 402 toward the second position. In some embodiments of the method, the step of ratcheting further comprises the steps of releasing the force on the activating lever 402 and allowing the activating lever spring 206 to move the activating lever 402 toward the first position.

In some embodiments, the invention provides a method comprising rotating the housing 236 and at least a portion of the driving rod 226 relative to the pair of opposing arms 252A, 252B and to the implant 838. In some embodiments, the housing 236 is rotatable about an axis 218 extending between the opposing arms 252A, 252B relative to the arms 252A, 252B and to the implant 838, and wherein at least a portion of the driving rod 226 is rotatable about the axis 218 extending between the opposing arms 252A, 252B relative to the pair of opposing arms 252A, 252B and to the implant 838. This method may further comprise activating a drive mechanism 224 wherein the activating step moves the implant distally and distracts the pair of opposing arms 252A, 252B. In some embodiments, inserting the implant comprises advancing the implant 838 into the distracted space between the vertebrae 880. In some embodiments, the advancing the implant comprises activating the drive mechanism 224 and extending the implant 838 beyond the distal end of the pair of opposing arms 252A, 252B.

In some embodiments, the invention provides a method comprising mounting the implant 838 to a driving rod 826 of a vertebral distractor-inserter 868 having a housing 136, a pair of opposing arms 852A, 852B, and a ratchet drive mechanism 224 in mechanical communication with the driving rod 826. The method further comprises positioning the distal end of the pair of arms 852A, 852B between the vertebrae 880, and distracting the vertebrae 880. Distracting the vertebrae 880 may further comprise activating the ratchet drive mechanism 224 and inserting the implant 838 between the distracted vertebrae 880. Inserting the implant 838 may comprise advancing the implant 838 into the distracted space between the vertebrae 880, wherein the step of advancing comprises activating the ratchet drive mechanism 224 and retracting the pair of opposing arms 852A, 852B from between the vertebrae 880.

In some embodiments of the method, the step of activating moves the implant 838 distally and distracts the pair of opposing arms 852A, 852B. In some embodiments, the distraction is caused by the distal motion of the implant 838 having a depth that is greater than the distance between the arms 852A, 852B at the distal end of the device 868. As the implant 838 moves distally, the implant 838 contacts the arms 852A, 852B and forces them apart, outwardly from the axis of the driving rod 826. When the arms 852A, 852B are forced apart, if the distal ends of the arms 852A, 852B are between the vertebrae 880, the distal motion of the implant 838 also distracts, i.e. opens, the space between the vertebrae 880.

Alternatively, in another embodiment, the implant interface 848 contacts the arms 852A, 852B, distracts the arms 852A, 852B, and thus distracts the vertebrae 880 as the interface 848 is moved distally. In some embodiments, the step of advancing comprises extending the implant 838 beyond the distal end of the pair of opposing arms 852A, 852B. In some embodiments, the activating the ratchet drive mechanism 224 comprises ratcheting the driving rod 826 distally, wherein the driving rod 826 comprises an axis 218 and a surface 366 with a plurality of angled ratchet teeth 210 on at least a portion of the surface 366, and wherein the ratchet drive mechanism 224 comprises an activating lever 202 capable of movement between a first position and a second position and mounted to the housing 136 by an activating lever pivot 204, a first ratchet pawl 232 coupled to the activating lever 202 and adapted to engage the ratchet teeth 210 and move the driving rod 826 distally relative to the housing 136, and a second ratchet pawl 260 adapted to engage the ratchet teeth 210 and oppose proximal motion of the driving rod 826 relative to the housing 136.

In some embodiments, the invention provides a method for ratcheting comprising the step of applying a force to the activating lever 202 to move the lever 202 toward the second position. In some embodiments the drive mechanism 224 comprises a handle 228 attached to the housing 136 and an activating lever spring 206 coupled to the activating lever 202 and the handle 228, wherein the activating lever spring 206 opposes proximal movement of the lever 202 relative to the handle 228, and wherein the step of ratcheting further comprises the steps of releasing the force on the activating lever 202 and allowing the activating lever spring 206 to move the activating lever 202 toward the first position. In some embodiments, the method comprises releasing the implant 838 from the distractor-inserter 868, wherein the implant 838 was coupled to the distractor-inserter 868.

In some embodiments, the invention provides a method comprising mounting the implant 838 to a driving rod 826 of a vertebral distractor-inserter 868 having a pair of opposing arms 852A, 852B having a distal end, a housing 136 in mechanical communication with the pair of opposing arms 852A, 852B which is rotatable about an axis 118 extending between the opposing arms 852A, 852B relative to the arms 852A, 852B and to the implant 838, and a drive mechanism 224 in mechanical communication with the driving rod 826, wherein the driving rod 826 extends through at least a portion of the housing 136 and between the pair of opposing arms 852A, 852B and wherein at least a portion of the driving rod 826 is rotatable about the axis 118 extending between the opposing arms 852A, 852B relative to the pair of opposing arms 852A, 852B and to the implant 838, positioning the distal end of the pair of arms 838 between the vertebrae 880, rotating the housing 136 and at least a portion of the driving rod 826 relative to the pair of opposing arms 852A, 852B and to the implant 838, distracting the vertebrae 880, inserting the implant 838 between the distracted vertebrae 880, and retracting the pair of opposing arms 852A, 852B from between the vertebrae 880. The distracting may further comprise activating the drive mechanism 224, wherein the activating moves the implant 838 distally and distracts the pair of opposing arms 852A, 852B. The inserting may comprise advancing the implant 838 into the distracted space between the vertebrae 880. The advancing may comprise activating the drive mechanism 224 and extending the implant 838 beyond the distal end of the pair of opposing arms 852A, 852B.

The method may further comprise ratcheting the driving rod 826 distally, wherein the driving rod 826 comprises an axis 118 and a surface 366 with a plurality of angled ratchet teeth 110 on at least a portion of the surface 366, and wherein the drive mechanism 224 comprises an activating lever 102 capable of movement between a first position and a second position and mounted to the housing 136 by an activating lever pivot 204, a first ratchet pawl 232 coupled to the activating lever 102 and adapted to engage the ratchet teeth 110 and move the driving rod 826 distally relative to the housing 136, and a second ratchet pawl 260 adapted to engage the ratchet teeth 110 and oppose proximal motion of the driving rod 826 relative to the housing 136. The ratcheting can comprise actions previously described herein.

The positioning can further comprise using a depth adjustor 642 to control the implantation depth between the vertebrae 880. Some embodiments of the method comprise mounting the implant 838 to a driving rod 826 of a vertebral distractor-inserter 868 having a pair of opposing arms 852A, 852B having a distal end and a depth guard 812, an implant depth adjustor 642 that is adjustable to a plurality of implant depth settings, a housing 136 in mechanical communication with the pair of opposing arms 852A, 852B, and a drive mechanism 224 in mechanical communication with the driving rod 826, wherein the driving rod 826 extends through at least a portion of the housing 136 and between the pair of opposing arms 852A, 852B, and wherein the mounting comprises the step of adjusting the implant depth adjustor 642 to control the maximum distal implant depth achievable during the inserting step, positioning the distal end of the pair of arms 852A, 852B between the vertebrae 880, wherein the positioning comprises urging the pair of arms 852A, 852B between the vertebrae 880 up to the position where the depth guard 812 contacts the vertebrae 880, distracting the vertebrae 880, inserting the implant 838 between the distracted vertebrae 880, and retracting the pair of opposing arms 852A, 852B from between the vertebrae 880.

In some embodiments, the invention provides a method for implanting an implant 838 between distracted vertebrae 880 comprising urging wherein the step of urging moves a pair of arms 852A, 852B between the vertebrae 880 up to a distal depth of at most about 75 mm, or at least about 25 mm, or between about 35 mm and 55 mm, wherein distal depth is the distance from a depth guard 812 to the distal end of the pair of opposing arms 852A, 852B. In some embodiments, the implant depth achievable is a maximum of about 25 mm, a minimum of about 0 mm, or between about 3 mm and 8 mm. The implant depth is measured from the distal end of the depth stop 846 to the distal end of the implant interface 848. In some embodiments, the distractor-inserter 868 is adapted to push the housing 136 proximally relative to the implant 838 upon insertion of the implant 838 to a selected implant depth setting, and the inserting comprises the step of retracting the pair of opposing arms 852A, 852B from between the vertebrae 880 by abutting the arm depth guard 812 against a proximal side of the vertebrae 880 and activating the drive mechanism 224.

In some embodiments, the invention provides a vertebral distractor-inserter, comprising a housing, a pair of opposing arms in mechanical communication with the housing, and a driving means for driving a rod and an implant at the distal end of the rod distally, wherein the driving means comprises an activating lever and a driving mechanism activated by the activating lever. The driving means may comprise a gripping means for gripping the rod while the activating lever drives the rod distally relative to the housing. Such means is described below and shown in FIGS. 4A & 4B. The driving means may comprise a ratcheting means for incrementally ratcheting the rod distally as the activating lever is pulled proximally relative to the housing. Examples of such ratcheting means are described herein and some example embodiments are shown in FIGS. 1, 2, and 3. The vertebral distractor-inserter may comprise a holding means for opposing proximal motion of the rod while resetting the lever after lever activation. Examples of such holding means are described herein. The vertebral distractor-inserter may comprise a rotating means for allowing operator rotation of the housing relative to the pair of opposing arms about an axis extending between the opposing arms. Examples of such rotating means are described herein, and examples are shown in FIGS. 1 and 5. The vertebral distractor-inserter may comprise a depth-controlling means for adjusting and controlling the depth to which an implant may be inserted by an operator between adjacent vertebrae. Examples of such depth-controlling means are described herein, and examples are shown in FIGS. 1, 2, 6, 7, and 8.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A vertebral distractor-inserter, comprising:
   (a) a pair of opposing arms;
   (b) a driving rod extending between the pair of opposing arms, wherein the driving rod comprises an axis and a surface with a plurality of angled ratchet teeth on at least a portion of the surface; and
   (c) a ratchet drive mechanism in mechanical communication with the driving rod;
   (d) wherein the ratchet drive mechanism is rotatable relative to the pair of opposing arms;
   further comprising a housing in mechanical communication with the pair of opposing arms, wherein the driving rod extends through at least a portion of the housing;
   wherein the ratchet drive mechanism comprises:
   (i) an activating lever mounted to the housing by an activating lever pivot;
   (ii) a first ratchet pawl coupled to the activating lever and adapted to engage the ratchet teeth and move the driving rod distally relative to the housing; and
   (iii) a second ratchet pawl adapted to engage the ratchet teeth and oppose proximal motion of the driving rod relative to the housing;
   wherein the surface of the driving rod comprises an area that is substantially free of ratchet teeth on a contiguous longitudinal surface of the driving rod, and wherein the driving rod is movable proximally relative to the housing upon rotation of the rod about its axis such that the ratchet pawls are in contact with the contiguous longitudinal surface that is free of ratchet teeth; and
   wherein the ratchet teeth disengage from the first and second ratchet pawls upon rotation of the driving rod about its axis.

2. The distractor-inserter of claim 1, comprising a handle attached to the housing.

3. The distractor-inserter of claim 1, wherein the ratchet drive mechanism comprises an activating lever spring coupled to the activating lever and the handle, wherein the activating lever spring opposes proximal movement of the lever relative to the handle.

4. The distractor-inserter of claim 1, the ratchet drive mechanism comprising:
   (a) a first pawl spring that opposes downward movement of the first pawl; and (b) a second pawl spring that opposes downward movement of the second pawl.

5. The distractor-inserter of claim 1, wherein the driving rod comprises a proximal end having a knob.

6. The distractor-inserter of claim 1, wherein the distractor-inserter is adapted for single-handed use.

7. The distractor-inserter of claim 1, wherein the driving rod comprises a distal end and an implant interface coupled to the distal end of the driving rod.

8. The distractor-inserter of claim 7, further comprising an implant in contact with the implant interface, whereby distal motion of the driving rod imparts distal motion to the implant through the implant interface; and distal motion of the implant forces the opposing arms apart.

9. The distractor-inserter of claim 8, wherein each opposing arm comprises an arm pivot.

10. The distractor-inserter of claim 9, wherein the pair of opposing arms comprises an arm spring.

11. The distractor-inserter of claim 10, wherein at least one opposing arm comprises an arm depth guard.

12. The distractor-inserter of claim 7, wherein the implant interface comprises an implant coupler.

13. A vertebral distractor-inserter, comprising:
(a) a pair of opposing arms;
(b) a housing in mechanical communication with the pair of opposing arms and rotatable relative to the pair of opposing arms about an axis extending between the opposing arms; and
(c) a driving rod extending through at least a portion of the housing and between the pair of opposing arms;
further comprising a ratchet drive mechanism in mechanical communication with the driving rod, wherein the driving rod comprises a surface with a plurality of angled ratchet teeth on at least a portion of the surface;
the ratchet drive mechanism comprising:
(i) an activating lever mounted to the housing by an activating lever pivot;
(ii) a first ratchet pawl coupled to the activating lever and adapted to engage the ratchet teeth and move the driving rod distally relative to the housing; and
(iii) a second ratchet pawl adapted to engage the ratchet teeth and oppose proximal motion of the driving rod relative to the housing;
wherein the surface of the driving rod comprises an area that is substantially free of ratchet teeth on a contiguous longitudinal surface of the driving rod, and wherein the driving rod is movable proximally relative to the housing upon rotation of the rod about its axis such that the ratchet pawls are in contact with the contiguous longitudinal surface that is free of ratchet teeth; and
wherein the ratchet teeth disengage from the first and second ratchet pawls upon rotation of the driving rod about its axis.

14. The vertebral distractor-inserter of claim 13, wherein the driving rod comprises a distal end having an implant interface, wherein the housing and at least a portion of the driving rod are rotatable relative to the pair of opposing arms and the implant interface.

15. The vertebral distractor-inserter of claim 14, wherein the implant interface comprises an interface rotation element, whereby the interface rotation element allows rod rotation relative to the pair of opposing arms.

16. The vertebral distractor-inserter of claim 15, wherein the housing comprises a housing rotation element, whereby the housing rotation element allows housing and rod rotation relative to the pair of opposing arms.

17. The vertebral distractor-inserter of claim 13, comprising a drive mechanism adapted to move the driving rod distally relative to the housing.

18. The distractor-inserter of claim 13, comprising a handle attached to the housing.

19. The distractor-inserter of claim 13, wherein the ratchet drive mechanism comprises an activating lever spring coupled to the activating lever and the handle, wherein the activating lever spring is opposes proximal movement of the lever relative to the handle.

20. The distractor-inserter of claim 13, wherein the driving rod comprises a proximal end having a knob.

21. The distractor-inserter of claim 13, wherein the distractor-inserter is adapted for single-handed use.

22. The distractor-inserter of claim 13, wherein the driving rod comprises a distal end and an implant interface coupled to the distal end of the driving rod.

23. The distractor-inserter of claim 22, further comprising an implant in contact with the implant interface, whereby distal motion of the driving rod imparts distal motion to the implant through the implant interface; and distal motion of the implant forces the opposing arms apart.

24. The distractor-inserter of claim 22, wherein each opposing arm comprises an arm pivot.

* * * * *